United States Patent

Miller et al.

Patent Number: 6,028,110
Date of Patent: Feb. 22, 2000

[54] SUCCINYL HYDROXAMIC ACID, N-FORMYL-N-HYDROXY AMINO CARBOXYLIC ACID AND SUCCINIC ACID AMIDE DERIVATIVES AS METALLOPROTEASE INHIBITORS

[75] Inventors: Andrew Miller; Raymond Paul Beckett; Fionna Mitchell Martin; Mark Whittaker, all of Cowley, United Kingdom

[73] Assignee: British Biotech Pharmaceuticals Ltd., United Kingdom

[21] Appl. No.: 08/737,981

[22] PCT Filed: May 26, 1995

[86] PCT No.: PCT/GB95/01226

§ 371 Date: Nov. 22, 1996

§ 102(e) Date: Nov. 22, 1996

[87] PCT Pub. No.: WO95/32944

PCT Pub. Date: Dec. 7, 1995

[30] Foreign Application Priority Data

May 28, 1994 [GB] United Kingdom .................. 9410802
Feb. 24, 1995 [GB] United Kingdom .................. 9503754

[51] Int. Cl.[7] .................. A61K 31/19; A61K 31/181; A61K 31/16; C07C 51/31
[52] U.S. Cl. .................. 514/575; 514/613; 514/614; 514/615; 514/620; 514/902; 514/825; 514/925; 514/575; 514/576; 530/331; 530/335; 530/336; 562/400; 562/495; 562/623; 562/543
[58] Field of Search .................. 562/621, 623, 562/400, 495, 543; 514/576, 575, 613, 614, 615, 620, 902, 825, 925; 530/331, 335, 336; 554/36, 37

[56] References Cited

U.S. PATENT DOCUMENTS

| | | | |
|---|---|---|---|
| 4,028,401 | 6/1977 | Fessler et al. | 260/500.5 H |
| 4,077,998 | 3/1978 | Fessler et al. | 260/518 R |
| 4,558,034 | 12/1985 | Galardy et al. | 514/7 |
| 4,599,361 | 7/1986 | Dickens et al. | 514/575 |
| 4,681,894 | 7/1987 | Murray et al. | 514/575 |
| 4,743,587 | 5/1988 | Dickens et al. | 514/575 |
| 5,114,953 | 5/1992 | Galardy et al. | 514/323 |
| 5,183,900 | 2/1993 | Galardy et al. | 548/495 |
| 5,256,657 | 10/1993 | Singh et al. | 514/228.2 |
| 5,270,326 | 12/1993 | Galardy et al. | 514/323 |
| 5,300,501 | 4/1994 | Porter et al. | 514/238.2 |

FOREIGN PATENT DOCUMENTS

| | | | |
|---|---|---|---|
| 489579 | 12/1991 | European Pat. Off. | C07C 259/06 |
| 489577 | 6/1992 | European Pat. Off. | C07C 259/06 |
| 575844 | 12/1993 | European Pat. Off. | C07C 259/06 |
| 613883 | 9/1994 | European Pat. Off. | C07C 259/06 |
| 9324475 | 9/1993 | WIPO | C07D 295/22 |
| 9324449 | 12/1993 | WIPO | C07C 237/22 |

*Primary Examiner*—Jose G. Dees
*Assistant Examiner*—Sabiha N. Qazi
*Attorney, Agent, or Firm*—Banner & Witcoff, Ltd.

[57] ABSTRACT

A pharmaceutical or veterinary composition comprising a compound of formula I

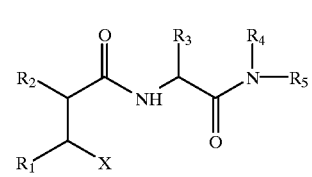

(I)

wherein X is a —$CO_2H$ group and $R_1$, $R_2$, $R_3$, $R_4$, $R_5$ are as defined in the specification, or a salt, hydrate or solvate thereof, and a pharmaceutically or veterinarily acceptable excipient or carrier. A method of treatment of diseases or conditions mediated by MMPs in mammals, such as rheumatoid arthritis, osteoarthritis, periodontitis, gingivitis, corneal ulceration or tumour invasion by secondary means, by administering to the mammal an effective amount of the composition.

16 Claims, No Drawings

SUCCINYL HYDROXAMIC ACID, N-FORMYL-N-HYDROXY AMINO CARBOXYLIC ACID AND SUCCINIC ACID AMIDE DERIVATIVES AS METALLOPROTEASE INHIBITORS

This application has been filed under 35 USC 371 as a national stage application of PCT/GB95/01226 filed May 26, 1995.

The present invention relates to therapeutically active hydroxamic acid, N-formyl-N-hydroxyamino and carboxylic acid derivatives, to processes for their preparation, to pharmaceutical compositions containing them, and to the use of such compounds in medicine. In particular, the compounds are inhibitors of gelatinases, which are metalloproteinases involved in tissue degradation.

BACKGROUND OF THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (L. M. Matrisian, *Trends in Genetics*, 1990, 6, 121–125).

The precise role of each of the various types of MMP in mediating different clinical disease conditions is not understood at present. However, there is some evidence that for some clinical end points individual MMP types may have a greater causative role than others. For the treatment of conditions mediated mainly by one MMP type, clearly it would be desirable to use an MMP inhibitor which selectively inhibited that MMP, or at least was significantly more potent as an inhibitor of that MMP than of other MMP types.

Many known MMP inhibitors are peptide derivatives, based on naturally occurring amino acids, and are analogues of the cleavage site in the collagen molecule. A recent paper by Chapman et al (J. Med. Chem. 1993, 36, 4293–4301) reports some general structure/activity findings in a series of N-carboxyalkyl peptides. Other known MMP inhibitors are less peptidic in structure, and may more properly be viewed as pseudopeptides or peptide mimetics. Such compounds usually having a functional group capable of binding to the active site zinc (II) ion in the MMP, and known classes include those in which the zinc binding group is a hydroxamic acid, carboxylic acid, sulphydryl, and oxygenated phosphorus (eg phosphinic acid and phosphonic acid) groups.

Three known classes of pseudopeptide or peptide mimetic MMP inhibitors have a hydroxamic acid group, an N-formyl-N-hydroxyamino, and a carboxylic acid group respectively as their zinc binding groups. With a few exceptions, such known MMPs may be represented by the structural formula (IA)

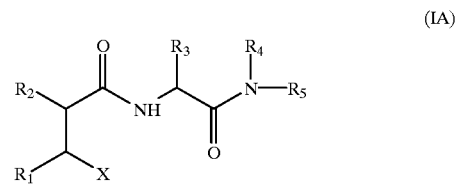

(IA)

in which X is the zinc binding hydroxamic acid (—CONHOH), N-formyl-N-hydroxyamino (—N(OH)CHO), or carboxylic acid (—COOH) group and the groups $R_1$ to $R_5$ are variable in accordance with the specific prior art disclosures of such compounds. The following patent publications disclose hydroxamic acid-based MMP inhibitors:

| | |
|---|---|
| US 4599361 | (Searle) |
| EP-A-2321081 | (ICI) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| WO 92/09563 | (Glycomed) |
| US 5183900 | (Glycomed) |
| US 5270326 | (Glycomed) |
| WO 92/17460 | (SmithKline Beecham) |
| EP-A-0489577 | (Celltech) |
| EP-A-0489579 | (Celltech) |
| EP-A-0497192 | (Roche) |
| US 5256657 | (Sterling Winthrop) |
| WO 92/13831 | (British Bio-technology) |
| WO 92/22523 | (Research Corporation Technologies) |
| WO 93/09090 | (Yamanouchi) |
| WO 93/09097 | (Sankyo) |
| WO 93/20047 | (British Bio-technology) |
| WO 93/24449 | (Celltech) |
| WO 93/24475 | (Celltech) |
| EP-A-0574758 | (Roche) |

The following patent publications disclose N-formyl-N-hydroxyamino-based MMP inhibitors:

| | |
|---|---|
| EP-A-0236872 | (Roche) |

The following patent publications disclose carboxylic acid-based MMP inhibitors:

| | |
|---|---|
| EP-A-0489577 | (Celltech) |
| EP-A-0489579 | (Celltech) |
| WO 93/24449 | (Celltech) |
| WO 93/24475 | (Celltech) |

It is generally understood in the art that for metalloproteinase inhibitors of formula (IA) variation of the zinc binding group X and the substituents $R_1$, $R_2$, $R_3$, $R_4$ and $R_5$ can have an appreciable effect on the potency of inhibition of the metalloproteinase enzymes. As mentioned, the group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase. The $R_1$, $R_2$ and $R_3$ groups are believed to occupy respectively the P1, P1' and P2' amino acid side chain binding sites for the natural enzyme substrate. Generally a larger $R_1$ substituent enhances activity against stromelysin, a relatively short chain ($C_1$–$C_6$)alkyl group (such as sec-butyl) at $R_2$ is preferred for activity against collagenase.

MMP inhibitors of formula (IA) which have a degree of selectivity for gelatinases (rather than for example the collagenases, stromelysins and PUMP) have been reported, Patent publications EP-A-489577, EP-A-489579, WO-A-93/24449 and WO-A-93/24475 (all by Celltech) disclose classes of compounds characterised inter alia by $R_2$ groups which are somewhat more extended than the short chain ($C_1$–$C_6$)alkyl $R_2$ groups preferred for collagenase inhibition. A typical preferred $R_2$ grouping of this known kind is 3-phenylpropyl. Patent publication, EP-A-575844 (Roche) discloses compounds which possess activity against both gelatinases and stromelysin. Compounds included within the general structural type disclosed in EP-A-575844, are permitted to have $R_2$ groups up to $C_{12}$ in length, but this appears to be the maximum extension contemplated or permitted by the prior art at the $R_2$ position, whether for gelatinase selective or non-gelatinase selective compounds.

BRIEF DESCRIPTION OF THE INVENTION

The present inventors have found that lengthwise extension of the $R_2$ group of MMP inhibitors of the general type represented by formula (I) to $C_{13}$ and longer, increases the degree of selectivity of the compounds for gelatinases relative to collagenases and stromelysins, compared with the corresponding MMP inhibitors with shorter chain $R_2$ groups.

The present invention therefore makes available a new class of gelatinase selective MMP inhibitors of the general formula (IA) type, which are principally distinguished from the prior art MMP inhibitors by the length of the $R_2$ group.

DETAILED DESCRIPTION OF THE INVENTION

The present invention provides compounds of general formula I

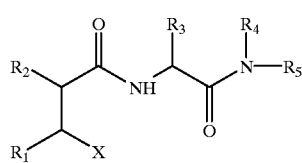

(I)

wherein
X is a —$CO_2H$, —N(OH)CHO or —CONHOH group;
$R_1$ is hydrogen; ($C_1$–$C_6$)alkyl; ($C_2$–$C_6$)alkenyl; phenyl; substituted phenyl; phenyl ($C_1$–$C_6$)alkyl); substituted phenyl ($C_1$–$C_6$)alkyl; heterocyclyl; substituted heterocyclyl; heterocyclyl($C_1$–$C_6$)alkyl; substituted heterocyclyl ($C_1$–$C_6$)alkyl; a group $BSO_nA$— wherein n is 0, 1 or 2 and B is hydrogen or a ($C_1$–$C_6$) alkyl, phenyl, substituted phenyl, heterocyclyl, ($C_1$–$C_6$)acyl, phenacyl or substituted phenacyl group, and A represents ($C_1$–$C_6$)alkyl; amino; protected amino; acylamino; OH, SH; ($C_1$–$C_6$) alkoxy; ($C_1$–$C_6$)alkylamino; di-($C_1$–$C_6$)alkylamino; ($C_1$–$C_6$)alkylthio; aryl ($C_1$–$C_6$)alkyl; amino($C_1$–$C_6$)alkyl; hydroxy($C_1$–$C_6$)alkyl, mercapto($C_1$–$C_6$)alkyl or carboxy ($C_1$–$C_6$)alkyl wherein the amino-, hydroxy-, mercapto- or carboxyl-group is optionally protected or the carboxyl-group amidated; lower alkyl substituted by carbamoyl, mono(lower alkyl)carbamoyl, di(lower alkyl)carbamoyl, di(lower alkyl)amino, or carboxy-lower alkanoylamino;
$R_2$ represents a linear saturated or unsaturated $C_{13}$–$C_{24}$ hydrocarbon chain, which chain
  (i) may be interrupted by one or more non-adjacent —O— or —S— atoms or —C(=O)—, —S(→O)—, —S(=O)$_2$— or —N($R_x$)— groups wherein $R_x$ is hydrogen, methyl or ethyl, provided that the maximum length of the chain is no more than 28 C, O, S and N atoms, and/or
  (ii) may be substituted with one or more groups selected from $C_1$–$C_6$ alkyl, OH, OMe, halogen, $NH_2$, $NHCH_3$, $N(CH_3)_2$, $CO_2H$, $CO_2CH_3$, $COCH_3$, CHO, $CONH_2$, $CONHCH_3$, $CON(CH_3)_2$, $CH_2OH$, $NHCOCH_3$, provided that the maximum length of the chain is no more than 28 C, O, S and N atoms;
$R_3$ is the characterising side chain of a natural or non-natural α amino acid in which any functional groups may be protected, with the proviso that $R_3$ does not represent hydrogen;
$R_4$ is hydrogen, $C_1$–$C_6$ alkyl, ($C_1$–$C_4$)perfluoroalkyl or a group D-($C_1$–$C_6$ alkyl) wherein D represents hydroxy, ($C_1$–$C_6$)alkoxy, ($C_1$–$C_6$)alkylthio, acylamino, optionally substituted phenyl or heteroaryl, $NH_2$, or mono- or di- ($C_1$–$C_6$ alkyl amino;
$R_5$ is hydrogen or a ($C_1$–$C_6$)alkyl group;
or a salt, hydrate or solvate thereof.

As used herein, the term "side chain of a natural or non-natural alpha amino acid" means the group R in a natural or non-natural amino acid of formula $H_2N$—CH(R)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Functional groups in such amino acid side chains may be protected; for example carboxyl groups may be esterified (for example as a $C_1$–$C_6$ alkyl ester), amino groups may be converted to amides (for example as a $COC_1$–$C_6$ alkyl amide) or carbamates (for example as a C(=O)$OC_1$–$C_6$ alkyl or C(=O)$OCH_2Ph$ carbamate), hydroxyl groups may be converted to ethers (for example a $C_1$–$C_6$ alkyl or a ($C_1$–$C_6$ alkyl)phenyl ether) or esters (for example a C(=O) $C_1$–$C_6$ alkyl ester) and thiol groups may be converted to thioethers (for example a tert-butyl or benzyl thioether) or thioesters (for example a C(=O)$C_1$–$C_6$ alkyl thioester).

Examples of side chains of non-natural alpha amino acids include those referred to below in the discussion of suitable $R_3$ groups for use in compounds of the present invention.

As used herein, the unqualified term "heterocyclyl" or "heterocyclic" means (i) a 5–7 membered heterocyclic ring containing one or more heteroatoms selected from S, N and O, and optionally fused to a benzene ring, including, for example pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3-methyl-2,5- dioxo-1-imidazolidinyl and 3,4,4-trimethyl-2,5-dioxo-1-imidazolidinyl, or (ii) a naphthalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

As used herein, the term "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be $(C_1-C_6)$alkoxy, hydroxy, mercapto, $(C_1-C_6)$alkylthio, amino, halo (including fluoro, chloro, bromo and iodo), trifluoromethyl, nitro, —COOH, —CONH$_2$, —COOR$^A$, —NHCOR$^A$ or —CONHR$^A$ wherein R$^A$ is a $(C_1-C_6)$alkyl group.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X group —S,
C atom carrying the $R_2$ group —R,
C atom carrying the $R_3$ group —S, but mixtures in which the above configurations predominate are also contemplated.

An advantage of the compounds of the invention is their relative specificity of inhibition of gelatinases relative to collagenases and stromelysins. For compounds of the invention, the minimum chain length of the $R_2$ group is 13 C atoms and the maximum chain length is 24 C atoms, or a total of 28 C, O, S and N atoms when optional O, S and N atoms are present in the chain. Thus chain lengths of (inter alia) from 13 to 20, 13 to 18, 13 to 16, 14 to 20, 14 to 18 and 14 to 16, specifically of 13, 14, 15, 16, 17 or 18 C and optional O,S, and N atoms are specifically useable. Thus:

$R_2$ may for example be tridecyl, tetradecyl, pentadecyl, hexadecyl, heptadecyl, octadecyl, nonadecyl, eicosyl, heneicosyl, docosyl, tricosyl, tetracosyl, 13-methoxytridecyl, 3-undecoxypropyl, 4-decoxybutyl, 5-nonoxypentyl, 6-octoxyhexyl, 7-heptaoxylheptyl, 8-hexaoxyoctyl. Presently preferred are compounds in which $R_2$ is tetradecyl, pentadecyl, hexadecyl or octadecyl.

As previously stated, the compounds of the invention are principally distinguished from the compounds disclosed in the prior art patent publications listed above by the identity of the group $R_2$. Accordingly, the groups $R_1$, $R_3$, $R_4$, and $R_5$ may include those which have been disclosed in the corresponding positions of compounds disclosed in any of those prior art patent publications listed above. Without limiting the generality of the foregoing, examples of substituents $R_1$, $R_3$, $R_4$, and $R_5$ are given below:

X is a —CO$_2$H, —N(OH)CHO or —CONHOH group. Compounds in which X is —COOH are especially preferred for their specificity in inhibiting gelatinases rather than collagenases or stromelysins.

$R_1$ may for example be hydrogen, methyl, ethyl, hydroxyl, allyl, or thienylsulphanylmethyl, thienylsulphinylmethyl, thienylsulphonylmethyl and phthalimidomethyl. Presently preferred are compounds in which $R_1$ is hydrogen, hydroxyl, allyl or phthalimidomethyl. Compounds in which $R_1$ is hydrogen are especially preferred for their specificity in inhibiting gelatinases rather than collagenases or stromelysins.

$R_3$ may for example be $(C_1-C_6)$alkyl, benzyl, hydroxybenzyl, benzyloxybenzyl, $(C_1-C_6)$alkoxybenzyl, or benzyloxy$(C_1-C_6)$alkyl group; or the characterising group of a natural α amino acid, in which any functional group may be protected, any amino group may be acylated and any carboxyl group present may be amidated; or a group -[Alk]$_n$R$_6$ where Alk is a $(C_1-C_6)$alkyl or $(C_2-C_6)$alkenyl group optionally interrupted by one or more —O—, or —S— atoms or —N(R$_7$)— groups [where R$_7$ is a hydrogen atom or a $(C_1-C_6)$alkyl group], n is 0 or 1, and R$_6$ is an optionally substituted cycloalkyl or cycloalkenyl group; or a benzyl group substituted in the phenyl ring by a group of formula —OCH$_2$COR$_8$ where R$_8$ is hydroxyl, amino, $(C_1-C_6)$alkoxy, phenyl$(C_1-C_6)$alkoxy, $(C_1-C_6)$alkylamino, di$((C_1-C_6)$alkyl)amino, phenyl$(C_1-C_6)$alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic$((C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl $(C_1-C_6)$alkyl, hydroxy, formyl, amino, $(C_1-C_6)$alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; or a group —CR$_a$R$_b$R$_c$ in which:
each of R$_a$, R$_b$ and R$_c$ is independently hydrogen, $(C_1-C_6)$alkyl, $(C_2-C_6)$alkenyl, $(C_2-C_6)$alkynyl, phenyl$(C_1-C_6)$alkyl, $(C_3-C_8)$cycloalkyl, the foregoing being subject to the proviso that R$_a$, R$_b$ and R$_c$ are not all hydrogen; or R$_c$ is hydrogen, $(C_1-C_6)$alkyl, $(C_2-C_6)$alkenyl, $(C_2-C_6)$alkynyl, phenyl$(C_1-C_6)$alkyl, or $(C_3-C_8)$cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently $(C_1-C_6)$alkyl, $(C_2-C_6)$alkenyl, $(C_2-C_6)$alkynyl, phenyl$(C_1-C_6)$alkyl, or a group as defined for R$_c$ below other than hydrogen, or $R_a$ and $R_b$ together with the carbon atom to which they are attached form a 3 to 8 membered cycloalkyl or a 3- to 8-membered heterocyclic ring, and $R_c$ is hydrogen, —OH, —SH, halogen, —CN, —$CO_2H$, $(C_1-C_4)$perfluoroalkyl, —$CH_2OH$, —$CO_2(C_1-C_6)$alkyl, —$O(C_1-C_6)$alkyl, —$O(C_2-C_6)$alkenyl, —$S(C_1-C_6)$alkyl, —SO$(C_1-C_6)$alkyl, —$SO_2(C_1-C_6)$ alkyl, —$S(C_2-C_6)$ alkenyl, —$SO(C_2-C_6)$alkenyl, —$SO_2(C_2-C_6)$ alkenyl or a group —Q—W wherein a represents a bond or —O—, —S—, —SO— or —$SO_2$— and W represents a phenyl, phenylalkyl, $(C_3-C_8)$cycloalkyl, $(C_3-C_8)$cycloalkylalkyl, $(C_4-C_8)$cycloalkenyl, $(C_4-C_6)$cycloalkenylalkyl, heteroaryl or heteroarylalkyl group, which group W may optionally be substituted by one or more substituents independently selected from, hydroxyl, halogen, —CN, —$CO_2H$, —$CO_2(C_1-C_6)$alkyl, —$CONH_2$, —$CONH(C_1-C_6)$ alkyl, —$CONH(C_1-C_6alkyl)_2$, —CHO, —$CH_2OH$, $(C_1-C_4)$perfluoroalkyl, —$O(C_1-C_6)$alkyl, —$S(C_1-C_6)$alkyl, —$SO(C_1-C_6)$alkyl, —$SO_2(C_1-C_6)$alkyl, —$NO_2$, —$NH_2$, —$NH(C_1-C_6)$alkyl, —$N((C_1-C_6)$alkyl$)_2$, —$NHCO(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl.

Examples of particular $R_3$ groups include benzyl, isobutyl or t-butyl, 1-benzylthio-1-methylethyl, 1-methylthio-1-methylethyl, and 1-mercapto-1-methylethyl. Presently preferred are compounds in which $R_3$ is benzyl, t-butyl or 1-mercapto-1-methylethyl.

$R_4$ may for example be $C_1-C_6$ alkyl, $(C_1-C_4)$perfluoroalkyl or a group D-$(C_1-C_6$ alkyl) wherein D represents hydroxy, $(C_1-C_6)$alkoxy, $(C_1-C_6)$alkylthio, acylamino, optionally substituted phenyl or heteroaryl. Examples of particular $R_4$ groups include methyl, ethyl, n- and isopropyl, n-, sec- and tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone) propyl, optionally substituted phenylethyl, phenylpropyl, phenylbutyl, or phenylpentyl. Presently preferred are compounds in which $R_4$ is hydrogen or methyl.

$R_5$ may for example be hydrogen, methyl or ethyl. Presently preferred are compounds in which $R_5$ is hydrogen.

Interesting compounds of the invention are:

3R-(1S-Methylcarbamoyl-2-phenyl-ethylcarbamoyl) nonadecanoic acid (dicyclohexylamine salt), 3R-(1S-Methylcarbamoyl-2-phenyl-ethylcarbamoyl)-nonadecanoic acid (free acid), 3R-(2,2-Dimethyl-1S-methylcarbamoyl-propylcarbamoyl)-nonadecanoic acid, 3R or S-(2-Mercapto-2-methyl-1S-methylcarbamoyl-propylcarbamoyl)-nonadecanoic acid, 3-(1S-tert-Butylcarbamoyl-2,2-dimethyl-propylcarbamoyl)-nonadecanoic acid (dicyclohexylamine salt), 3-(2,2-Dimethyl-1S-isopropylcarbamoyl-propylcarbamoyl)-nonadecanoic acid (dicyclohexylamine salt), 3-(1S-Dimethylcarbamoyl-2,2-dimethyl-propylcarbamoyl)-nonadecanoic acid (potassium salt), 3-(2-Methyl-1S-methylcarbamoyl-2-methylsulfanyl-propylcarbamoyl)-nonadecanoic acid, 3-(2-Benzylsulfanyl-2-methyl-1S-methylcarbamoyl-propylcarbamoyl)-nonadecanoic acid, 3-(1S-Methylcarbamoyl-2-phenyl-ethylcarbamoyl)-heptadecanoic acid, 3-(1S-Methylcarbamoyl-2-phenyl-ethylcarbamoyl)-octadecanoic acid, 3-(1S-Carbamoyl-2,2-dimethyl-propylcarbamoyl)-nonadecanoic acid, 3-(2,2-Dimethyl-1S-methylcarbamoyl-propylcarbamoyl)-heptadecanoic acid, 3-(2,2-Dimethyl-1S-methylcarbamoyl-propylcarbamoyl)-octadecanoic acid, 2R-Hexadecyl-$N^4$-hydroxy-$N^1$-(1S-methylcarbamoyl-2-phenylethyl)-succinamide, $N^1$-(2,2-Dimethyl-1S-methylcarbamoyl-propyl)-2R-hexadecyl-$N^4$-hydroxy-succinamide, $N^1$-(1S-tert-Butylcarbamoyl-2,2-dimethyl-propyl)-2-hexadecyl-$N^4$-hydroxy-succinamide, 2-Hexadecyl-$N^4$-hydroxy-$N^1$(1S-isopropylcarbamoyl-2,2-dimethyl-propyl)-succinamide, $N^1$-(1S-Dimethylcarbamoyl-2,2-dimethyl-propyl)-2-hexadecyl-$N^4$-hydroxy-succinamide, $N^4$-Hydroxy-$N^1$-(1S-methylcarbamoyl-2-phenyl-ethyl)-2-tetradecyl-succinamide, 2R or S-[(Formyl-hydroxy-amino)-methyl]-octadecanoic acid (2,2-dimethyl-1S-methylcarbamoyl-propyl)-amide, and salts, solvates or hydrates thereof.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises:

(a) causing an acid of general formula (II)

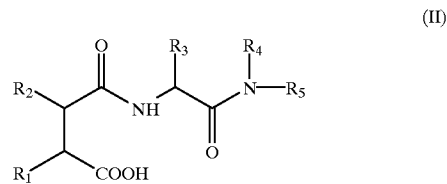
(II)

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

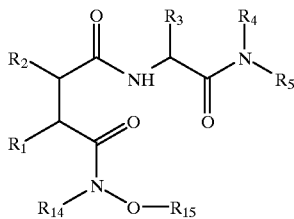

(IIb)

in which $R_1$, $R_2$, $R_3$, $R_4$, and $R_5$ are as defined in general formula (I), $R_{14}$ is an amino protecting group and $R_{15}$ is a hydroxyl protecting group.

For method (a) conversion of (II) to an activated derivative such as the pentafluorophenyl, hydroxy-succinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

In method (a) in the special case where $R_1$ in compound (I) is hydroxy, a particularly useful technique may be reaction of hydroxylamine with a dioxalone of formula (IIa):

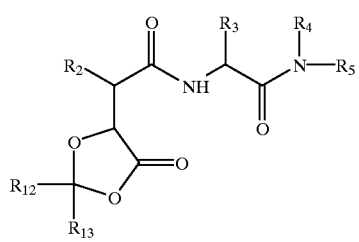

(IIa)

wherein the groups $R_{12}$ and $R_{13}$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the present invention in which X is a carboxylic acid group —COOH may be prepared by a process comprising: coupling an acid of formula (III) or an activated derivative thereof with an amine of formula (IV)

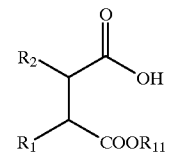

(III)

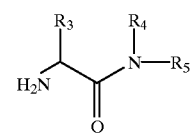

(IV)

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, $R_4$, and $R_5$.

Compounds of formula (IIb) may be prepared by a process comprising: causing an acid of formula (IIIa) or an activated derivative thereof to react with an amine of formula (IV)

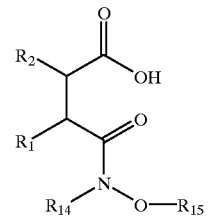

(IIIa)

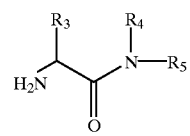

(IV)

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, $R_{14}$ is an amino protecting group and $R_{15}$ is a hydroxyl protecting group as referred to in connection with formula (IIb) above, and subsequently removing any protecting groups from $R_1$ $R_2$, $R_3$, $R_4$, and $R_5$.

Active derivatives of acids (III) and (IIa) include activated esters such as the pentafluorophenyl ester, acid anhydrides and acid halides, eg chlorides. Suitable hydroxy protecting groups $R_{11}$ may be selected from those known in the art.

Amine intermediates of formula (IV) are either known compounds or may be prepared from known amino acid starting materials using standard methods and by analogy with the specific preparative examples herein.

In the special case where $R_1$ in compound (III) or (IIIa) is hydroxy, it too may be protected during the coupling of compounds (III) or (IIIa) and (IV). In the case where $R_1$ is hydroxy in compound (III) a particularly useful technique may be simultaneous protection of the two hydroxy groups as a dioxalone of formula (V):

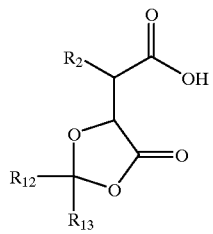
(V)

wherein the groups $R_{12}$ and $R_{13}$ are derived from a dioxalone forming reagent, and may be, for example, hydrogen, alkyl, phenyl or substituted phenyl.

Compounds of the invention in which X is an N-formyl-N-hydroxyamino (—N(OH)CHO) group may be prepared by deprotecting an N-protected N-formyl-N-hydroxyamino compound of formula (IIc):

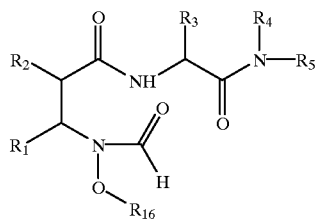
(IIc)

in which $R_1$, $R_2$, $R_3$, $R_4$, and $R_5$ are as defined in general formula (I) and $R_{16}$ is a group convertible to a hydroxy group by hydrogenolysis or hydrolysis. Benzyl is a preferred $R_{16}$ group for removal by hydrogenolysis, and tetrahydropyranyl is a preferred group for removal by acid hydrolysis.

Compounds of formula (IIc) may be prepared by a process comprising: causing an acid of formula (IIIb) or an activated derivative thereof to react with an amine of formula (IV)

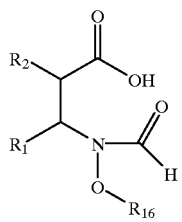
(IIIb)

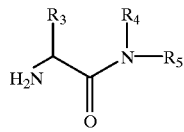
(IV)

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{16}$ is a group convertible to a hydroxy group by hydrogenolysis or hydrolysis as referred to in connection with formula (IIc) above, and optionally removing protecting groups from $R_1$, $R_2$, $R_3$, $R_4$, and $R_5$.

Compounds of formula (IIIb) may be prepared by N-formylation, for example using acetic anhydride and formic acid, of compounds of formula (IIIc)

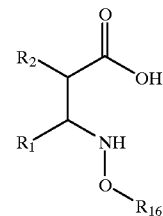
(IIIc)

wherein $R_1$, $R_2$ and $R_{16}$ are as defined in relation to formula (IIIb).

As mentioned above, compounds of formula (I) are useful in human or veterinary medicine since they are active as inhibitors of MMPs, particularly gelatinases.

Accordingly in another aspect, this invention concerns:
(i) a method of management (by which is meant treatment or prophylaxis) of diseases or conditions mediated by MMPs in mammals, in particular in humans, which method comprises administering to the mammal an effective amount of a compound as defined with respect to formula (I) above, or a pharmaceutically acceptable salt thereof; and
(ii) a compound as defined with respect to formula (I) for use in human or veterinary medicine, particularly in the management (by which is meant treatment or prophylaxis) of diseases or conditions mediated by MMPs; and
(iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases.

In a further aspect of the invention there is provided a pharmaceutical or veterinary composition comprising a compound of formula (I) together with a pharmaceutically or veterinarily acceptable excipient or carrier. In view of the oral bioavailability advantages of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The examples which follow illustrate embodiments of the invention but are not intended to limit the scope in any way. The amino acids used in the examples were commercially available or were prepared according to literature procedures.

The following abbreviations have been used throughout:

| | |
|---|---|
| DCHA | Dicyclohexylamine |
| DIPE | Diisopropyl ether |
| DMF | N,N-Dimethylformamide |
| EDC | N-Ethyl-N'-(3-dimethylaminopropyl)carbodiimide hydrochloride |
| HOBt | 1-Hydroxybenzotriazole |
| TFA | Trifluoroacetic acid |

$^1$H and $^{13}$C NMR spectra were recorded using a Bruker AC 250E spectrometer at 250.1 and 62.9 MHz, respectively. Elemental microanalyses were performed by CHN Analysis Ltd. (Alpha House, Countesthorpe Road, South Wigston, Leicester LE8 2PJ, UK) or Medac Ltd. (Department of Chemistry, Brunel University, Uxbridge, Middlesex UB8 3PH).

EXAMPLE 1

3R-(1S-Methylcarbamoyl-2-phenyl-ethylcarbamoyl) nonadecanoic acid (dicyclohexylamine salt)

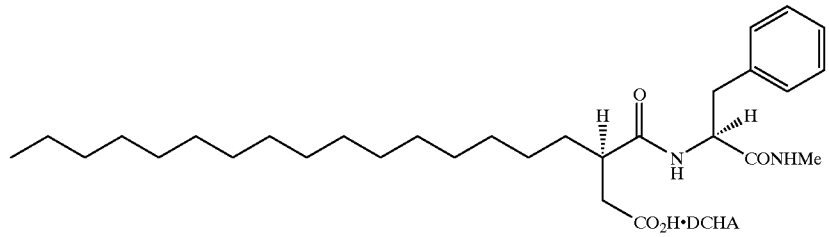

Step A

2R-Hexadecyl-succinic acid-4-tert-butyl ester 1-(2,3,4,5,6-pentafluorophenyl)ester 2R-Hexadecyl-succinic acid-4-tert-butyl ester (prepared by methods analogous to those described in WO 92/13831) (10.0 g, 25.1 mmol) was dissolved in dichloromethane (500 ml) and the solution was stirred and cooled to 0° C. during the addition of pentafluorophenol (6.0 g, 32.6 mmol) and EDC (5.8 g, 30.3. mmol). The reaction mixture was allowed to warm to room temperature and then stirred overnight. The solution was diluted with more dichloromethane (100 ml) and washed successively with water, 1M sodium carbonate (×2), 1M hydrochloric acid and finally with water. The organic phase was dried over anhydrous sodium sulphate, filtered and concentrated in vacuo. The residual oil was purified by flash column chromatography (silica gel, 4% ethyl acetate in hexane) to yield the desired product (8.9 g, 66%) as a white amorphous solid; $^1$H NMR: δ (CDCl$_3$), 3.16

(1H, m), 2.77 (1H, dd, J=9.3, 16.9 Hz), 2.52 (1H, dd, J=5.2, 16.9 Hz), 1.89–1.61 (2H, m), 1.54–1.18 (28H, m), 0.89 (3H, t, J=6.6 Hz).

Step B
3R-(1S-Methylcarbamoyl-2-phenyl-ethylcarbamoyl)-nonadecanoic acid tert-butyl ester 2R-Hexadecyl-succinic acid-4-tert-butyl ester 1-(2,3,4,5,6-pentafluorophenyl)ester (4.0 g, 7.5 mmol) was dissolved in DMF (50 ml) and L-phenylalanine N-methylamide (1.3 g, 7.3 mmol) was added. The reaction mixture was stirred overnight at room temperature, then the solvent was removed by evaporation under reduced pressure. The residue was dissolved in dichloromethane (400 ml) and the solution was washed successively with water (200 ml), 1M sodium carbonate (2×150 ml), 1M hydrochloric acid (200 ml) and finally with water. The organic phase was dried over anhydrous sodium sulphate, filtered and concentrated in vacuo. The residue was purified by flash column chromatography (silica gel, 5% methanol in dichloromethane) to yield the desired product contaminated with a small amount of DMF. The product was dissolved in dichloromethane (200 ml) and the solution was washed with water (3×100 ml) dried over anhydrous sodium sulphate, filtered and evaporated to leave the title compound (3.21 g, 81%) as a pale yellow foam; $^1$H NMR: δ (CDCl$_3$), 7.29–7.13 (5H, m), 6.69–6.55 (2H, m), 4.64 (1H, m), 3.07 (2H, d, J=7.1 Hz), 2.67 (3H, d, J=4.8 Hz), 2.59–2.27 (3H, m) 1.59–1.09 (30H, m), 1.40 (9H, s), 0.86 (3H, d, J=6.6 Hz).

Step C
3R-(1S-Methylcarbamoyl-2-phenyl-ethylcarbamoyl)-nonadecanoic acid (dicyclohexylamine salt)

3R-(1S-Methylcarbamoyl-2-phenyl-ethylcarbamoyl)-nonadecanoic acid tert-butyl ester (3.21 g, 6.0 mmol) was dissolved in dichloromethane (30 ml) and TFA (30 ml) and the mixture was stored at 0° C. overnight. The solvents were removed under reduced pressure and the residual TFA was removed by repeated azeotroping with toluene. The remaining gum (500 mg, 1.05 mmol) was treated with a 0.2 M solution of dicyclohexylamine in ethyl acetate (5.3 ml, 1.06 mmol) and left for ten minutes. The product crystallised spontaneously from solution and was collected by filtration and recrystallised from ethyl acetate to give the title compound (230 mg, 30%) as a white crystalline solid. m.p. 95° C. $^1$H NMR; δ ((CD$_3$)$_2$SO), 8.08–8.00 (2H, m), 7.14–7.09 (5H, m), 4.35 (1H, m), 3.04 (1H, dd, J=4.5, 13.7 Hz), 2.94–2.84 (2H, m), 2.81 (1H, dd, J=10.2, 13.4 Hz), 2.53 (3H, J=4.2 Hz), 2.48–2.39 (1H, m), 2.25 (1H, dd, J=8.3, 15.3 Hz), 2.05 (1H, dd, J=5.4, 15.4 Hz), 1.96–1.88 (4H, m), 1.75–1.16 (4H, m), 1.61–1.52 (2H, m), 1.38–0.90 (40H, m), and 0.84 (3H, t, J=6.7 Hz). $^{13}$C NMR; δ ((CD$_3$)$_2$SO), 174.2, 171.4, 138.4, 129.0, 127.9, 126.0, 54.1, 52.0, 42.7, 38.2, 37.1, 32.2, 31.3, 30.3, 29.0, 28.7, 26.6, 25.5, 25.2, 24.2, 22.1 and 13.9.

EXAMPLE 2

3R-(1S-Methylcarbamoyl-2-phenyl-ethylcarbamoyl)-nonadecanoic acid (free acid)

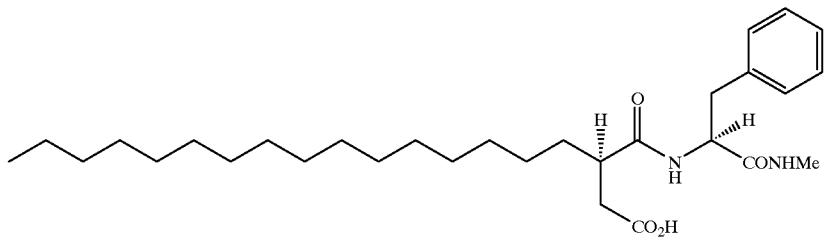

3R-(1S-Methylcarbamoyl-2-phenyl-ethylcarbamoyl)-nonadecanoic acid benzyl ester (prepared by a method analogous to that described in Example 1 (2.25 g, 3.80 mmol) was suspended in ethanol (50 ml) and placed under a blanket of argon. 10% palladium on charcoal was added as a slurry in ethanol (10 ml) and the mixture was stirred under an atmosphere of hydrogen gas for 6 hours. The system was purged with argon before removing the catalyst by filtration and washing thoroughly with a mixture of dichloromethane and methanol. The combined filtrate and washings were evaporated under reduced pressure and the residue was crystallised from a mixture of DIPE, ethanol and hexane to give the title compound as a white solid (1.5 g, 79%). m.p. 152° C. $^1$H NMR: δ (CDCl$_3$), 7.48 (1H, d, J=8.5 Hz), 7.30–7.10 (5H, m), 6.37–6.24 (1H, m), 4.75–4.62 (1H, m), 3.12–2.91 (2H, m), 2.66 (3H, d, J=4.8 Hz), 2.76–2.38 (2H, m), 1.69–1.37 (2H, m), 1.36–1.11 (28H, m) and 0.88 (3H, t, J=6.6 Hz). $^{13}$C NMR: δ (CDCl$_3$), 17.7, 173.3, 138.1, 129.1, 127.9, 126.1, 53.9, 41.6, 37.4, 36.4, 32.1, 31.3, 29.0, 28.7, 26.4, 25.4, 22.1 and 13.9. IR (KBr) $v_{max}$ 3297, 2856, 1732 and 1416 cm$^{-1}$. Found C 71.02, H 9.75, N 5.81%; $C_{30}H_{50}N_2O_4$.0.3 H$_2$O requires C 70.91, H 10.04, N 5.51%.

The following additional compounds of Examples 3 to 14 were prepared from the appropriate starting materials according to the method of Example 1:

EXAMPLE 3

3R-(2,2-Dimethyl-1S-methylcarbamoyl-propylcarbamoyl)-nonadecanoic acid

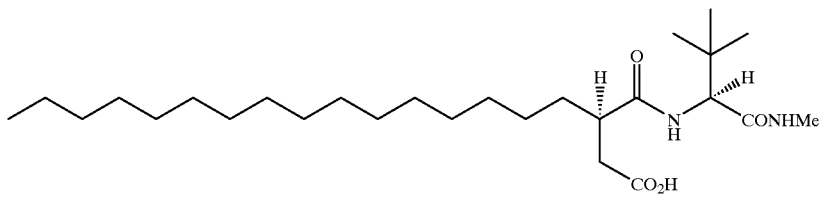

White amorphous solid. $^1$H NMR; δ (CDCl$_3$), 7.50 (1H, m), 7.25 (1H, m), 4.49 (1H, d, J=9.4 Hz), 2.85–2.61 (2H, m), 2.77 (3H, d, J=4.4 Hz), 2.43 (1H, m), 1.69–1.48 (2H, m), 1.36–1.10 (28H, m), 0.96 (9H, s) and 0.88 (3H, t, J=6.6 Hz). $^{13}$C NMR; δ (CDCl$_3$), 175.8, 175.5, 172.1, 60.4, 42.4, 36.5, 34.6, 32.8, 31.9, 29.7, 29.3, 27.2, 26.5, 26.0, 22.6 and 14.0.

EXAMPLE 4

3R or S-(2-Mercapto-2-methyl-1S-methylcarbamoyl-propylcarbamoyl)-nonadecanoic acid

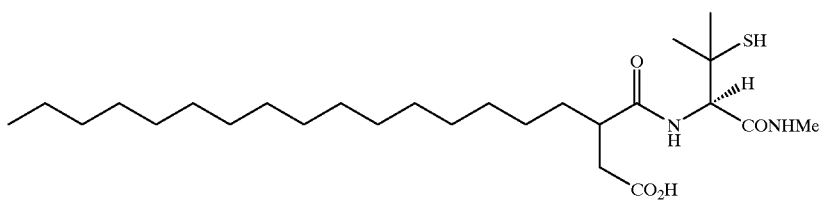

Two diastereoisomers separated by column chromatography

Isomer A

Colourless oil. $^1$H NMR; δ (CDCl$_3$), 7.22 (1H, d, J=9.3 Hz), 6.96 (1H, d, J=4.8 Hz), 4.55 (1H, d, J=9.3 Hz), 3.23–2.44 (6H, m), 1.59–0.97 (36H, br m) and 0.88 (3H, t, J=6.5 Hz). $^1$H NMR; δ (CDCl$_3$), 176.1, 175.3, 170.5, 60.3, 45.8, 42.5, 36.2, 32.7, 31.9, 30.8, 29.7, 29.5, 29.4, 28.3, 27.1, 26.1, 22.7 and 14.11. IR (CDCl$_3$): ν$_{max}$ 3311, 2920, 2854, 1708, 1650, 1512 cm$^{-1}$. Found C 64.08, H 10.57, N 5.75%; C$_{26}$H$_{50}$N$_2$O$_4$S requires C 64.16, H 10.35, N 5.76%.

Isomer B

Colourless foam. $^1$H NMR; δ (CDCl$_3$), 7.23 (1H, d, J=9.3 Hz), 7.00 (1H, d, J=4.8 Hz), 4.57 (1H, d, J=9.3 Hz), 2.84–2.44 (6H, m), 1.69–1.25 (36H, br m) and 0.88 (3H, t, J=6.5 Hz). $^{13}$C NMR; δ (CDCl$_3$), 176.0, 175.3, 170.5, 60.5, 45.9, 42.5, 36.2, 32.7, 31.9, 30.8, 29.7, 29.5, 29.3, 28.3, 27.1, 26.1, 22.7 and 14.1. IR (CDCl$_3$) ν$_{max}$ 2920, 2854, 1708, 1655 and 1507 cm$^{-1}$. Found C 63.90, H 10.25, N 5.74%; C$_{26}$H$_{50}$N$_2$O$_4$S requires C 64.16, H 10.35, N 5.76%.

EXAMPLE 5

3-(1S-tert-Butylcarbamoyl-2,2-dimethyl-propylcarbamoyl)-nonadecanoic acid (dicyclohexylamine salt)

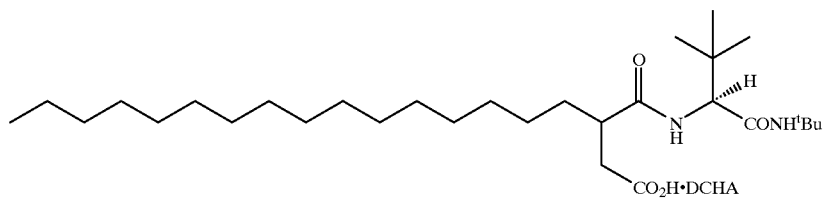

White powder. m.p. 111.5–11 9.5° C. $^1$H NMR; δ ((CD$_3$)$_2$SO), 7.61 (1H, d, J=9.9 Hz), 7.29 (1H, s), 4.01 (1H, d, J=9.7 Hz), 2.62–2.40 (3H, m), 2.20 (1H, dd, J=8.1, 16.5 Hz), 2.01 (1H, dd, J=5.4, 16.5 Hz), 1.74–1.35 (8H, m), 1.25–0.93 (53H, m), 0.74 (9H, s) and 0.71 (3H, t, J=6.7 Hz). $^{13}$C NMR; δ ((CD$_3$)$_2$SO), 176.0, 172.6 168.4, 58.5, 50.8, 48.8, 40.4, 32.9, 31.2, 29.9, 27.9, 27.7, 27.4, 27.1, 25.4, 25.3, 24.4, 23.2, 20.9 and 12.6. IR (KBr) ν$_{max}$ 3312, 2932, 2849, 1635, 1540, 1451, 1386, 1220 cm$^-$. Found: C 72.69, H 11.89, N 6.04%; C$_{42}$H$_{81}$N$_3$O$_4$.0.1 H$_2$O requires C 72.59, H 11.52, N 6.05%.

EXAMPLE 6

3-(2,2-Dimethyl-1S-isopropylcarbamoyl-propylcarbamoyl)-nonadecanoic acid (dicyclohexylamine salt)

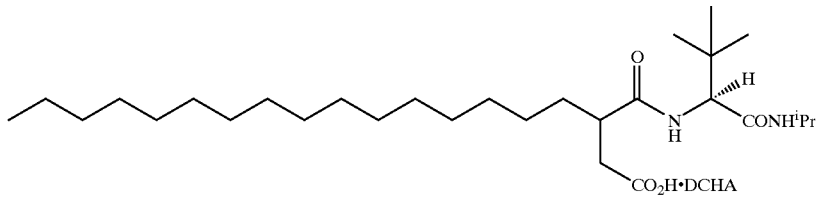

White solid. 57.5–60° C. $^1$H NMR; δ ((CD$_3$)$_2$SO), 7.68 (1H, d, J=9.7 Hz), 7.60 (1H, d, J=7.7 Hz), 4.0 (1H, d, J=9.7 Hz), 3.98–3.65 (1H, m), 2.58–2.52 (3H, m), 2.16 (1H, dd, J=8.3, 16.1 Hz), 1.99 (1H, dd, J=5.3, 16.0 Hz), 1.75–1.35 (8H, m), 1.30–0.85 (43H, m), 0.88 (6H, d, J=6.4 Hz), 0.74 (9H, s) and 0.71 (3H, t, J=6.8 Hz). $^{13}$C NMR; δ ((CD$_3$)$_2$SO), 174.1, 173.9, 169.0, 106.5, 59.7, 52.0, 41.9, 34.1, 32.2, 31.7, 31.3, 29.2, 29.0, 28.9, 28.7, 26.7, 25.5, 24.4, 22.2, 22.1 and 13.9. IR (KBr): $v_{max}$ 3300, 2932, 2849, 1641, 1546, 1457, 1392 and 1388 cm$^{-1}$. Found C 71.32, H 11.72, N 6.06%; C$_{41}$H$_{79}$N$_3$O$_4$.0.7 H$_2$O requires C 71.30, H 11.73, N 6.08%.

EXAMPLE 7

3-(1S-Dimethylcarbamoyl-2,2-dimethyl-propylcarbamoyl)-nonadecanoic acid (potassium salt)

30.0, 29.7, 29.4, 27.5, 26.6, 22.7 and 14.1. IR (KBr): $v_{max}$ 2919, 2849, 1625, 1572, 1508, 1467, 1396 and 1143 cm$^{-1}$. Found C 63.74, H 10.26, N 5.24%; C$_{28}$H$_{53}$N$_2$O$_4$K.0.4 H$_2$O requires C 63.69, H 10.27, N 5.31%

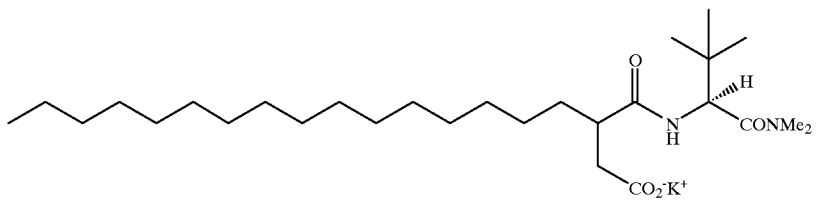

White powder. m.p. 93.5–101° C. $^1$H NMR; δ (CDCl$_3$), 8.94 (1H, d, J=9.0 Hz), 4.86 (1H, d, J=9.1 Hz), 3.16 (3H, s), 2.89 (3H, s), 2.54 (1H, m), 2.47–2.30 (2H, m), 1.78–1.65 (1H, m), 1.60–1.38 (1H, m), 1.35–1.17 (28H, m), 0.96 (9H, s) and 0.89 (3H, t, J=6.3 Hz). $^{13}$C NMR; δ (CDCl$_3$), 179.1, 176.4, 172.3, 54.5, 43.9, 40.6, 38.4, 35.5, 35.4, 32.5, 31.9,

EXAMPLE 8

3-(2-Methyl-1S-methylcarbamoyl-2-methylsulfanyl-propylcarbamoyl)-nonadecanoic acid

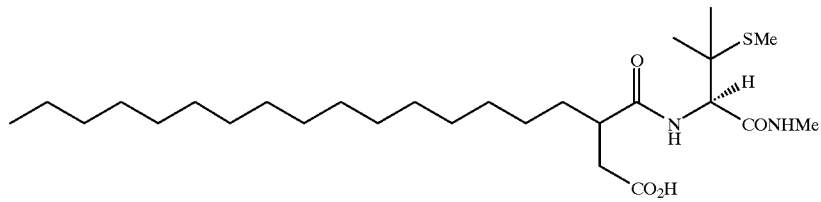

Colourless oil. $^1$H NMR; δ (CDCl$_3$), 7.20 (1H, d, J=8.7 Hz), 6.62 (1H, d, J=4.9 Hz), 4.57 (1H, d, J=8.8 Hz), 2.83 (3H, d, J=4.8 Hz), 2.85–2.70 (2H, m), 2.60–2.48 (1H, m), 2.09 (3H, s), 1.70–1.40 (2H, br m), 1.34 (3H, s), 1.36–1.20

(31H, m) and 0.89 (3H, t, J=6.6 Hz). $^{13}$C NMR; δ (CDCl$_3$), 175.4, 175.3, 170.1, 136.4, 112.6, 76.7, 58.2, 46.3, 42.4, 36.3, 32.3, 31.8, 29.6, 29.5, 29.4, 29.2, 27.1, 26.3, 25.4, 24.5, 22.5, 14.0 and 11.4. IR (CDCl$_3$) $v_{max}$ 2920, 2849, 1708, 1659 and 1510 cm$^{-1}$.

EXAMPLE 9

3-(2-Benzylsulfanyl-2-methyl-1S-methylcarbamoyl-propylcarbamoyl)-nonadecanoic acid

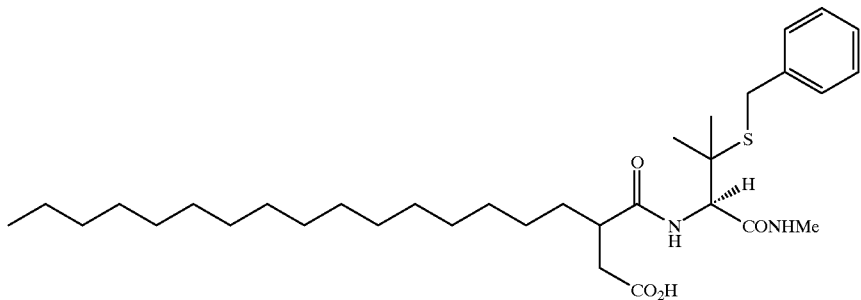

Colourless oil. $^1$H NMR; δ (CDCl$_3$), 7.35–7.25 (5H, m), 7.18 (1H, d, J=8.9 Hz), 6.11 (1H, d, J=4.9 Hz), 4.60 (1H, d, J=8.8 Hz), 3.84 (2H, dd, J=12.6, 3.0 Hz), 2.82–2.48 (6H, br m), 1.70–1.40 (2H, br m), 1.43 (3H, s), 1.32–1.20 (31H, m) and 0.89 (3H, t, J=6.5 Hz). $^{13}$C NMR; δ (CDCl$_3$), 175.5, 175.4, 170.2, 112.7, 77.2, 58.3, 46.4, 42.5, 36.4, 32.4, 31.9, 29.7, 29.7, 29.6, 29.5, 29.4, 27.2, 26.4, 25.5, 24.6, 22.7, 14.1 and 11.5. IR (CDCl$_3$): $v_{max}$ 2924, 2853, 1710, 1663 and 1512 cm$^{-1}$.

EXAMPLE 10

3-(1S-Methylcarbamoyl-2-phenyl-ethylcarbamoyl)-heptadecanoic acid

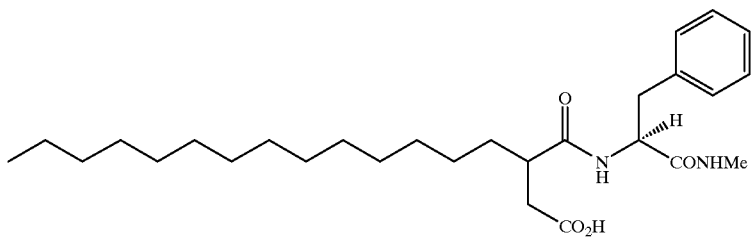

White powder. m.p. 154.5–156° C. $^1$H NMR; δ (CDCl$_3$), 7.40 (1H, br m), 7.27–7.11 (5H, m), 6.11 (1H, br m), 4.65 (1H, m), 3.11–2.90 (2H, m), 2.76–2.57 (2H, br m), 2.66 (3H, d, J=4.8 Hz), 2.45 (1H, m), 1.64 (1H, m), 1.44 (1H, m), 1.35–1.13 (24H, m) and 0.89 (3H, t, J=6.3 Hz). $^{13}$C NMR; δ (CDCl$_3$), 175.0, 174.3, 171.4, 137.0, 129.2, 128.4, 126.7, 54.6, 42.7, 37.9, 36.6, 32.1, 31.8, 29.6, 29.4, 29.4, 29.2, 27.2, 26.0, 22.6 and 14.0. IR (KBr) $v_{max}$ 3319, 2919, 2849, 2355, 1719, 1649, 1596, 1543, 1467, 1390, 1183 and 697 cm$^-$. Found C 71.10, H 10.03, N 5.58%; $C_{28}H_{46}N_2O_4$ requires C 70.85, H 9.77, N 5.90%.

EXAMPLE 11

3-(1S-Methylcarbamoyl-2-phenyl-ethylcarbamoyl)-octadecanoic acid

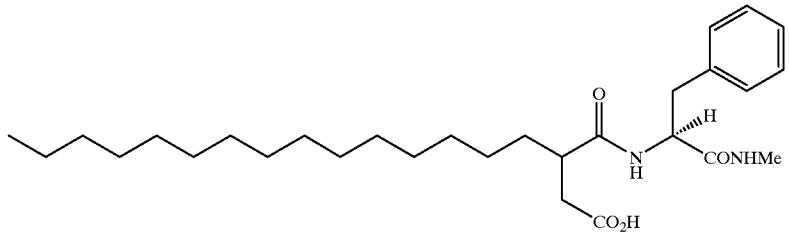

White powder. m.p. 149.5–152.5° C. $^1$H NMR; δ (CDCl$_3$), 7.41 (1H, d, J=8.4 Hz), 7.28–7.10 (5H, m), 6.14 (1H, br d), 4.67 (1H, m), 3.13–2.93 (2H, m), 2.76–2.58 (2H, br m), 2.66 (3H, d, J=4.8 Hz), 2.45 (1H, m), 1.65 (1H, br m), 1.44 (1H, br m), 1.36–1.10 (26H, m) and 0.89 (3H, t, J=6.3 Hz). $^{13}$C NMR; δ (CDCl$_3$), 175.4, 175.2, 172.0, 136.6, 129.1, 128.6, 55.1, 42.6, 38.5, 36.7, 32.4, 31.9, 29.7, 29.5, 29.4, 27.3, 26.2, 22.7 and 14.1. IR (KBr) ν$_{max}$ 3295, 2919, 2849, 1719, 1702, 1643, 1543, 1461, 1408, 1167 and 697 cm$^{-1}$. Found C 70.88, H 9.95, N 5.59%; C$_{29}$H$_{48}$N$_2$O$_4$ requires C 71.27, H 9.90, N 5.73%.

Colourless oil. $^1$H NMR; δ (CDCl$_3$), 7.28 (1H, d, J=9.3 Hz), 6.45 (1H, d, J=5.0 Hz), 5.25 (1H, br s), 4.37 (1H, d, J=9.6 Hz), 2.82 (3H, d, J=4.7 Hz), 2.77–2.69 (2H, m), 2.52 (1H, m), 1.78–1.38 (2H, m), 1.35–1.12 (24H, m) 0.97 (9H, s) and 0.89 (3H, t, J=6.5 Hz). $^{13}$C NMR; δ (CDCl$_3$), 175.7, 175.6, 171.8, 60.5, 42.4, 36.4, 34.7, 32.7, 32.4, 31.9, 29.7, 29.6, 29.5, 29.4, 28.0, 27.2, 26.5, 26.2, 22.7 and 14.1.

EXAMPLE 12

3-(1S-Carbamoyl-2,2-dimethyl-propylcarbamoyl)-nonadecanoic acid

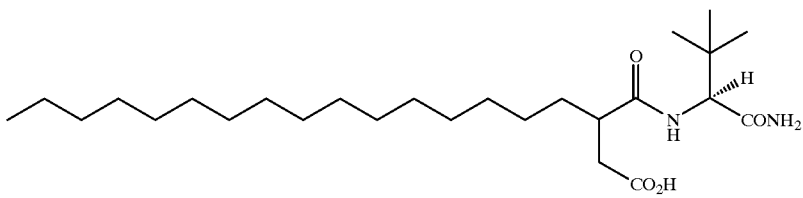

White solid. $^1$H NMR; δ (CD$_3$OD), 7.60 (1H, d, J=9.5 Hz), 4.20 (1H, d, J=9.4 Hz), 2.72 (1H, m), 2.56–2.24 (2H, br m), 1.55–1.05 (30H, m), 0.91 (9H, s) and 0.79 (3H, t, J=6.5 Hz). $^{13}$C NMR; δ (CD$_3$OD), 177.3, 175.6, 175.2, 61.7, 61.6, 43.8, 37.8, 35.2, 34.0, 33.1, 30.8, 30.6, 30.5, 28.2, 27.2, 23.7 and 14.5.

EXAMPLE 13

3-(2,2-Dimethyl-1S-methylcarbamoyl-propylcarbamoyl)-heptadecanoic acid

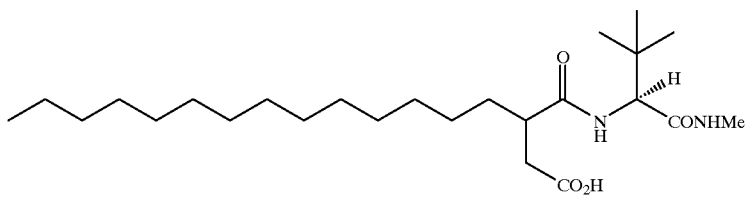

EXAMPLE 14

3-(2,2-Dimethyl-1S-methylcarbamoyl-propylcarbamoyl)-octadecanoic acid

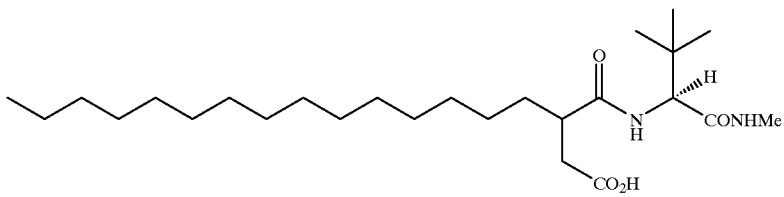

White foam. $^1$H NMR; δ (CDCl$_3$), 7.49 (1H, d, J=9.4 Hz), 7.12 (1H, d, J=9.4 Hz), 7.12 (1H, d, J=4.6 Hz), 4.50 (1H, d, J=9.5 Hz), 2.79–2.68 (5H, m), 2.49 (1H, m), 1.70–1.38 (2H, br m), 1.35–1.17 (26H, m), 0.96 (9H, s) and 0.88 (3H, t, J=6.6 Hz). $^{13}$C NMR; δ (CDCl$_3$), 175.4, 175.4, 171.9, 60.5, 42.4, 36.7, 34.8, 32.8, 32.0, 29.8, 29.7, 29.6, 29.4, 27.3, 26.6, 26.1, 22.7 and 14.1.

EXAMPLE 15

2R-Hexadecyl-N$^4$-hydroxy-N$^1$-(1S-methylcarbamoyl-2-phenylethyl)-succinamide

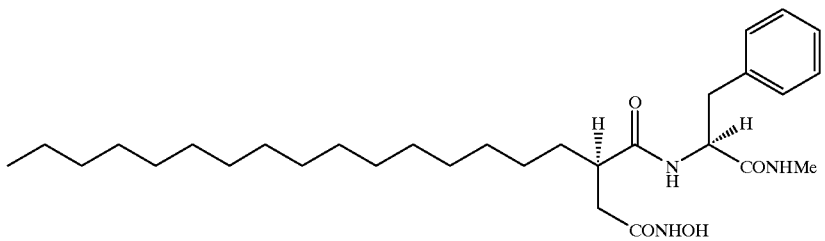

Step A
N$^4$-Benzyloxy-2R-hexadecyl-N$^1$-(1-methylcarbamoyl-2-phenylethyl)-succinamide 3R-(1S-Methylcarbamoyl-2-phenyl-ethylcarbamoyl) nonadecanoic acid (2.42 g, 4.8 mmol) was dissolved in dichloromethane (250 ml) and the solution was stirred and cooled to 0° C. during the addition of HOBt (1.0 g, 7.4 mmol) followed by EDC (1.5 g, 7.8 mmol). The reaction mixture was stirred at 0° C. for 20 minutes then allowed to warm to room temperature and stirred overnight. O-benzylhydroxylamine (1.3 g, 9.6 mmol) was then added and the reaction was stirred for a further 24 hours. The reaction mixture was diluted with chloroform (200 ml) and washed with water, 1M hydrochloric acid, 1M sodium carbonate and finally with water. An insoluble precipitate was formed in the organic phase and this was removed by filtration and found to be intermediate 1-hydroxybenzotriazolyl active ester (the filtrate contained only cyclised material). The active ester (1.5 g, 2.5 mmol) was redissolved in DMF (30 ml) and treated with more O-benzylhydroxylamine (616 mg, 5 mmol) and stirred overnight at room temperature. The resulting white precipitate was removed by filtration, washed with ethyl acetate and dried under high vacuum. Yield: 1.2 g (41%). $^1$H NMR; δ (CDCl$_3$), 8.08 (1H, br m), 7.91–7.82 (1H, m), 7.41–7.31 (5H, m), 7.28–7.12 (5H, m), 4.40 (1H, m), 3.32 (2H, s), 3.01 (1H, dd, J=6, 16 Hz), 2.81 (1H, dd, J=9, 16 Hz), 2.58 (3H, d, J=5 Hz), 2.03 (1H, dd, J=9, 16 Hz), 1.91 (1H, dd, J=9, 16 Hz), 1.37–0.97 (30H, m) and 0.86 (3H, t, J=6.6 Hz).

Step B
2R-Hexadecyl-N$^4$-hydroxy-N$^1$-(1-methylcarbamoyl-2-phenylethyl)-succinamide N$^4$-Benzyloxy-2R-hexadecyl-N$^1$-(1-methylcarbamoyl-2-phenylethyl)-succinamide (1.2 g, 2.1 mmol) was suspended in ethanol and placed under a blanket of argon. 10% Palladium on charcoal was added and the mixture was stirred overnight under an atmosphere of hydrogen. The catalyst was removed by filtration and washed with DMF (150 ml). The filtrate was concentrated in vacuo to give a glassy solid which was recrystallised once from ethyl acetate. The product was dissolved in hot chloroform-methanol and filtered to remove traces of catalyst. The solvents were removed to leave the title compound (200 mg, 14%) as a white crystalline solid. m.p. 157° C. $^1$H NMR; δ ((CD$_3$)$_2$SO), 8.74 (1H, br s), 8.00 (1H, d, J=8.3 Hz), 7.87 (1H, m), 7.24–7.10 (5H, m), 4.44 (1H, br m), 3.02 (1H, dd, J=5.1, 13.8 Hz), 2.80 (1H, dd, J=9.7, 13.7 Hz), 2.55 (3H, d, J=4.4 Hz), 2.51–2.43 (1H, m), 2.04 (1H, dd, J=7.2, 14.4 Hz), 1.92 (1H, dd, J=7.5, 14.4 Hz), 1.36–0.92 (30H, m), and 0.84 (3H, t, J=6.8 Hz). $^{13}$C NMR; δ ((CD$_3$)$_2$SO), 173.7, 171.3, 167.7, 138.3, 129.0, 128.7, 127.9, 126.0, 54.0, 42.5, 37.2, 35.0, 31.8, 31.3, 29.0, 28.7, 26.5, 25.5, 22.1 and 13.9.

The following additional compounds of Examples 16–20 were prepared according to the method of Example 15:

EXAMPLE 16

N$^1$-(2,2-Dimethyl-1S-methylcarbamoyl-propyl)-2R-hexadecyl-N$^4$-hydroxy-succinamide

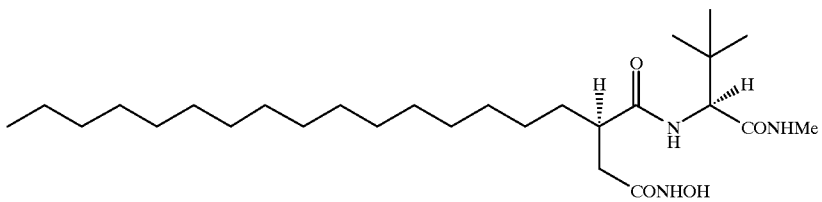

White amorphous solid. $^1$H NMR; δ (CD$_3$OD), 8.10–8.00 (1H, m), 7.87 (1H, d, J=9.3 Hz), 4.27 (1H, d, J=9.3 Hz), 2.92 (1H, m), 2.73 (3H, d, J=4.5 Hz), 2.37 (1H, dd, J=7.9, 14.5 Hz), 2.21 (1H, dd, J=6.5, 14.6 Hz), 1.65–1.13 (30H, m), 0.99 (9H, s) and 0.90 (3H, t, J=6.5 Hz). $^{13}$C NMR; δ (CD$_3$OD), 176.8, 173.2, 170.6, 62.0, 43.8, 36.6, 35.3, 33.5, 33.1, 30.8, 30.7, 30.5, 28.2, 27.2, 26.1, 23.7 and 14.5. IR (nujol mull), ν$_{max}$ 3313, 2431 cm$^{-1}$. Found C 65.45, H 10.75, N 8.80%; C$_{27}$H$_{53}$N$_3$O$_4$.0.6 H$_2$O requires C 65.57, H 11.05, N 8.50%.

EXAMPLE 17

N$^1$-(1S-tert-Butylcarbamoyl-2,2-dimethyl-propyl)-2-hexadecyl-N$^4$-hydroxy-succinamide

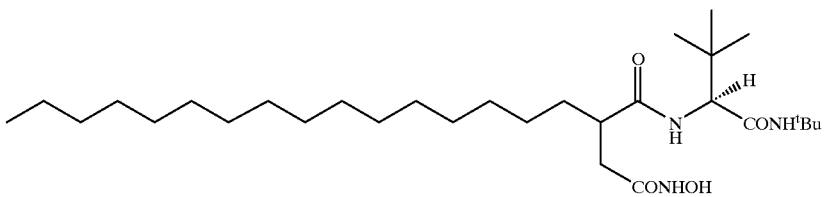

White powder. ca. 1:1 mixture of diastereoisomers. 173–175° C. $^1$H NMR; δ (CDCl$_3$), 6.80–6.65 (1H, m), 6.32 (0.5H, s), 6.13 (0.5H, s), 3.95 (0.5H, d, J=9.4 Hz), 3.93 (0.5H, d, J=9.0 Hz), 2.54–2.37 (1H, m), 2.31–2.00 (2H, m), 1.56–1.34 (1H, m), 1.34–1.17 (1H, m), 1.15 (4.5H, s), 1.14 (4.5H, s), 1.14–1.03 (28H, m), 0.81 (4.5H, s), 0.80 (4.5H, s), and 0.70 (3H, t, J=6.4 Hz). $^{13}$C NMR; δ (CDCl$_3$), 173.9, 173.8, 169.5, 169.3, 168.2, 167.8, 60.6, 60.5, 60.2, 50.7, 50.6, 42.8, 42.6, 35.5, 34.0, 33.8, 31.9, 31.6, 31.3, 28.7, 28.1, 28.1, 26.8, 26.7, 26.4, 26.2, 22.1, 13.6 and 13.2. IR (KBr) ν$_{max}$ 3295, 2919, 2849, 1637, 1543, 1465, 1390, 1381, 1261 and 1220 cm$^{-1}$. Found C 68.11, H 11.32, N 7.90%; C$_{30}$H$_{59}$N$_3$O$_4$.0.2 H$_2$O requires C 68.06, H 11.31, N 7.94%.

EXAMPLE 18

2-Hexadecyl-N$^4$-hydroxy-N$^1$(1S-isopropylcarbamoyl-2,2-dimethyl-propyl)-succinamide

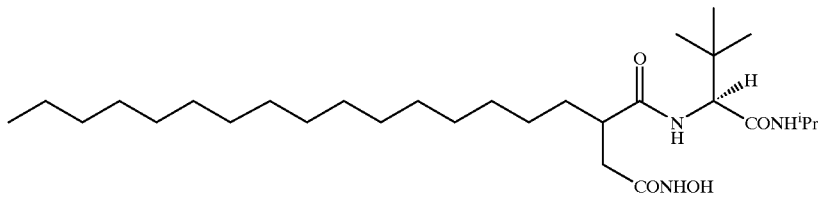

White powder. 88.5–90° C. $^1$H NMR; δ (CDCl$_3$), 8.13 (1H, br m), 6.86 (1H, d, J=9.4 Hz), 6.63 (1H, d, J=7.9 Hz), 4.01 (1H, d, J=9.4 Hz), 3.80 (1H, m), 2.50 (1H, m), 2.22 (1H, dd, J=8.0, 14.6 Hz), 2.02 (1H, dd, J=5.7, 14.7 Hz), 1.40 (1H, m), 1.22 (1H, m), 1.12–0.96 (28H, m), 0.92 (3H, d, J=6.6 Hz), 0.91 (3H, d, J=6.5 Hz), 0.77 (9H, s) and 0.67 (3H, t, J=6.3 Hz). $^{13}$C NMR; δ (CDCl$_3$), 173.8, 168.9, 167.8, 72.1, 59.9, 42.7, 40.5, 35.5, 34.0, 31.7, 31.3, 29.0, 28.9, 28.7, 28.1, 26.7, 26.2, 22.0, 22.0, 21.9 and 13.6. IR (KBr) $v_{max}$ 3307, 2919, 2849, 1637, 1537, 1461 and 1367 cm$^{-1}$. Found C 67.33, H 11.30, N 8.15%; $C_{29}H_{57}N_3O_4 \cdot 0.3$ $H_2O$ requires C 67.35, H 11.23, N 8.12%.

EXAMPLE 19

$N^1$-(1S-Dimethylcarbamoyl-2,2-dimethyl-propyl)-2-hexadecyl-$N^4$-hydroxysuccinamide

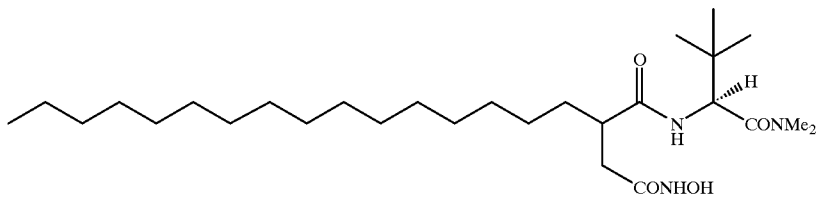

White powder. 165–166° C. $^1$H NMR; δ (CDCl$_3$), 9.69 (1H, br m), 6.80 (1H, d, J=9.6 Hz), 4.88 (1H, d, J=9.3 Hz), 3.15 (3H, s), 2.97 (3H, s), 2.86–2.70 (1H, m), 2.57–2.44 (1H, m), 2.34 (1H, dd, J=4.3, 14.3 Hz), 1.65 (1H, br), 1.46 (1H, br m), 1.36–1.14 (28H, m), 0.97 (9H, s) and 0.89 (3H, t, J=6.2 Hz). $^{13}$C NMR; δ (CDCl$_3$), 174.7, 171.3, 168.4, 54.5, 43.6, 38.4, 35.7, 35.7, 35.5, 32.6, 31.9, 29.7, 29.6, 29.5, 29.4, 27.2, 26.4, 22.7 and 14.1. IR (KBr) $v_{max}$ 3248, 3072, 2919, 2849, 1625, 1543, 1461 and 1384 cm$^{-1}$. C 67.49, H 11.09, N 8.54%; $C_{28}H_{55}N_3O_4$ requires C 67.56, H 11.14, N 8.44%.

EXAMPLE 20

$N^4$-Hydroxy-$N^1$-(1S-methylcarbamoyl-2-phenyl-ethyl)-2-tetradecyl-succinamide

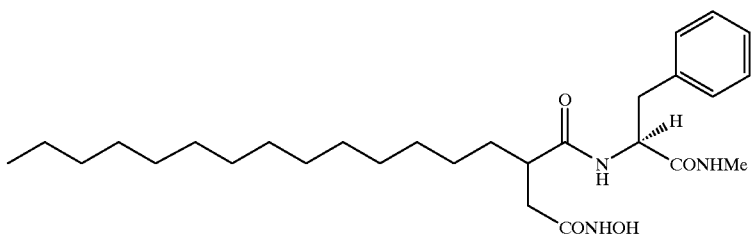

White solid. 4:1 mixture of diastereoisomers. $^1$H NMR; δ (CD$_3$OD, major diastereoisomer), 7.27 (0.5H, br s, partial exchange), 7.29–7.04 (5H, m), 4.40 (1H, dd, J=6.6, 8.8 Hz), 3.05 (1H, dd, J=6.6, 13.6 Hz), 2.82 (1H, dd, J=8.8, 13.6 Hz) 2.76–2.58 (2H, br m), 2.66 (3H, d, J=4.8 Hz), 2.57 (3H, s), 2.49 (1H, m), 2.13 (1H, dd, J=8.1, 14.6 Hz), 1.99 (1H, dd, J=6.8, 14.6 Hz), 1.25–0.90 (26H, m) and 0.80 (3H, t, J=6.4 Hz). $^{13}$C NMR; δ (CD$_3$OD), 177.0, 173.9, 130.3, 129.4, 127.7, 56.3, 38.9, 38.8, 36.3, 33.4, 33.0, 30.7, 30.6, 30.6, 30.5, 30.4, 30.3, 28.1, 26.3, 23.6, 16.2 and 14.3.

EXAMPLE 21

2R or S-[(Formyl-hydroxy-amino)-methyl]-octadecanoic acid (2,2-dimethyl-1S-methylcarbamoyl-propyl)-amide

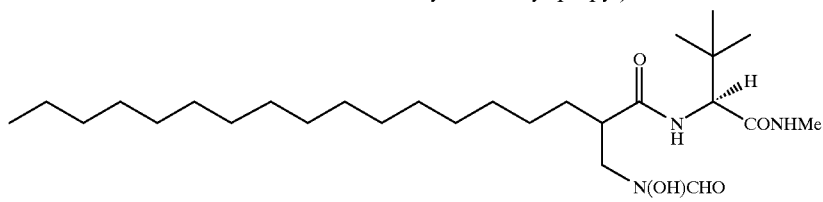

Step A

2-Hexadecyl-acrylic acid

To a solution of n-hexadecylmalonic acid (5 g, 15.2 mmol) in ethanol (30 ml) was added piperidine (1.5 ml, 15.2 mmol) followed by 37% aqueous formaldehyde solution (4.6 ml, 60.9 mmol). A white precipitate was formed. The reaction mixture was heated overnight at reflux whereupon some solid still remained. Additional ethanol (60 ml) was added and the reaction mixture was again heated at reflux overnight to afford a clear solution. The solvents were removed under reduced pressure, 1M hydrochloric acid (50 ml) and brine (50 ml) were added and the mixture was extracted three times with ethyl acetate. The combined extracts were washed with brine (50 ml), dried over anhydrous sodium sulphate, filtered and the solvent was removed under reduced pressure to afford the title compound (3.97 g, 88%) as a white solid. $^1$H NMR; δ (CD$_3$OD), 6.08 (1H, d, J=1.6 Hz), 5.51 (1H, J=1.6 Hz), 2.24 (2H, dt, J=1.6, 6.3 Hz), 1.25 (28H, br s), 0.86 (3H, t, J=6.6 Hz).

Step B

2RS-(Benzyloxy-amino-methyl)-octadecanoic acid

2-Hexadecyl-acrylic acid (3.0 g, 10 mmol) was dissolved in O-benzyl hydroxylamine (4 g, 32 mmol) and the mixture was heated at 80° C. overnight. The mixture was diluted with dichloromethane (30 ml) and the solution was washed with 1M hydrochloric acid (2×20 ml), dried over anhydrous magnesium sulphate filtered and evaporated to a white amorphous solid (4.43 g, crude) which was used in Step C without further purification. $^1$H NMR; δ (CDCl$_3$), 8.50 (2H br s), 7.37–7.32 (5H, m), 4.88 (2H, m), 3.42–3.10 (2H, br m), 2.91 (1H, br m), 1.78–1.35 (2H, br m), 1.30–1.20 (28H, m), 0.89 (3H, t, J=6.5 Hz).

Step C

2RS-[(Formyl-hydroxy-amino)-methyl]-octadecanoic acid

2RS-(Benzyloxy-amino-methyl)-octadecanoic acid (4.43 g, 10.5 mmol) was dissolved in formic acid (6 ml) and acetic anhydride (2 ml) was added dropwise. The reaction mixture was stirred overnight at room temperature, diluted with dichloromethane (50 ml), washed successively with water (50 ml) and brine (50 ml), dried over anhydrous sodium sulphate and filtered. The solvent was removed under reduced pressure to leave the title compound as a crude oil (4.3 g) which was used directly in the next step.

Step D

2RS-[(Formyl-hydroxy-amino)-methyl]-octadecanoic acid-(2,3,4,5,6-pentafluorophenyl)ester To an ice cooled solution of 2RS-[(Formyl-hydroxy-amino)-methyl]-octadecanoic acid (4.3 g, 9.6 mmol) in dichloromethane (50 ml) was added pentafluorophenol (1.84 g, 10 mmol) followed by EDC (1.92 g, 10 mmol). The mixture was allowed to warm slowly to room temperature then stirred overnight. The solution was washed successively with 1M sodium carbonate (2×50 ml), 1M hydrochloric acid (2×50 ml) and brine, dried (anhydrous sodium sulphate) and filtered. The solvent was evaporated under reduced pressure to leave an oil which was purified by column chromatography (silica gel, dichloromethane). Yield: 4.0 g (68%). $^1$H NMR; 67 (CDCl$_3$, rotamers), 8.16 (0.8H, s), 7.90 (0.2H, s), 7.43–7.30 (5H, m), 5.30 (2H, s), 3.12 (1H, br m), 2.46 (1H, m), 2.31 (1H, m), 1.90–1.55 (2H, m), 1.28 (28H, m), 0.91 (3H, t, J=6.3 Hz).

Step E 2R or S-[(Benzyloxy-formyl-amino)-methyl]-octadecanoic acid (2,2-dimethyl-1-methylcarbamoyl-propyl)-amide 2RS-[(Formyl-hydroxy-amino)-methyl]-octadecanoic acid-(2,3,4,5,6-pentafluorophenyl)ester (4 g, 6.5 mmol) and tert-leucine-N-methylamide (0.86 g 6.0 mmol) were dissolved together in DMF (20 ml) and stirred overnight at 35° C. The solvent was removed under reduced pressure and the residue was dissolved in dichloromethane (50 ml), washed successively with 1M sodium carbonate (2×25 ml), 1M hydrochloric acid (2×25 ml) and brine, dried (anhydrous sodium sulphate) and filtered. The solvent was removed under reduced pressure and the residue was purified by column chromatography (silica gel, 5% methanol in dichloromethane) to afford the title compound (1.75 g, 47%) as a colourless oil (1:1 mixture of diastereoisomers). $^1$H NMR; δ (CDCl$_3$), 8.15 (1H, br m), 7.35 (5H, m), 4.95–4.68 (2H, br m), 4.15 (1H, br m), 3.90–3.55 (3H, br m), 2.78 (3H, m), 2.70–2.44 (2H, m), 1.30–1.15 (28H, m), 0.99 (4.5H, s), 0.96 (4.5H, s) and 0.88 (3H, d, J=6.5 Hz).

The diastereoisomers were separated by column chromatography (silica gel, 60% ethyl acetate in hexane) before proceeding to Step F.

Step F 2R or S-[(Formyl-hydroxy-amino)-methyl]-octadecanoic acid (2,2-dimethyl-1S-methylcarbamoyl-propyl)-amide The benzyl protected hydroxamic acids prepared in Step E were individually deprotected by catalytic hydrogenolysis, according to the method described in Example 15 (Step B)

Isomer A

White solid. $^1$H NMR; δ (CDCl$_3$, 3:7 mixture of rotamers), 8.38 (0.3H, s), 7.82 (0.7H, s), 7.10 (0.3H, m), 6.95 (1H, d, J=9.6 Hz), 6.72 (0.7H, m), 4.36 (1d, J=9.6 Hz), 4.05 (0.3H, m), 3.81 (0.7H, dd, J=14.1, 9.8 Hz), 3.47 (1H, m), 2.91 (1H, m), 2.78 (3H, d, J=4.5 Hz), 1.53 (2H, m), 1.24 (28H, br s), 0.97 (2.7H, s), 0.94 (6.3H, s) and 0.87 (3H, t, J=6.2 Hz). $^{13}$C NMR; δ (CDCl$_3$), 175.3, 171.5, 171.0, 157.0, 60.5, 52.1, 44.3, 34.3, 31.8, 30.4, 30.1, 29.6, 29.4, 29.2, 27.1, 26.4, 25.9, 22.7, 22.5, 20.3 and 14.0. IR (CDCl$_3$), $v_{max}$ 3457, 3320, 3118, 2930, 2854, 1662, 1518, 1467, 1370, 1235, 1184 cm$^{-1}$.

Isomer B

White foam. $^1$H NMR; δ (CDCl$_1$, 1:1 mixture of rotamers), 8.33 (0.5H, s), 7.77 (0.5H, s), 7.49 (0.5H, m), 7.04 (0.5H, d, J=9.1 Hz), 6.92 (0.5H, d, J=8.2 Hz), 6.82 (0.5H, m), 4.31 (1H, d, J=8.81 Hz), 3.68 (1H, m), 3.61 (0.5H, m), 3.46 (0.5H, dd, J=14.3, 4.2 Hz), 2.93 (1H, m), 2.77 (3H, d, J=4.9 Hz), 1.63 (1H, m), 1.42 (1H, m), 1.25 (28H, br s), 1.01 (4.5H, s), 0.99 (4.5H, s) and 0.87 (3H, t, J=6.3 Hz). $^{13}$C NMR; δ (CDCl$_3$), 175.0, 173.6, 172.4, 171.3, 162.6, 157.3, 61.6, 60.8, 45.0, 44.7, 34.2, 33.3, 31.8, 29.5, 29.2, 27.2, 26.6, 26.1, 22.5 and 14.0. IR (CDCl$_3$), $v_{max}$ 3455, 3317, 2921, 2854, 1670, 1514, 1467, 1370 and 1236 cm$^{-1}$.

Comparative Example A

For comparison with the compound of Example 1 above the following compound was prepared similarly:

3R-(1S-Methylcarbamoyl-2-phenyl-ethylcarbamoyl)-pentadecanoic acid

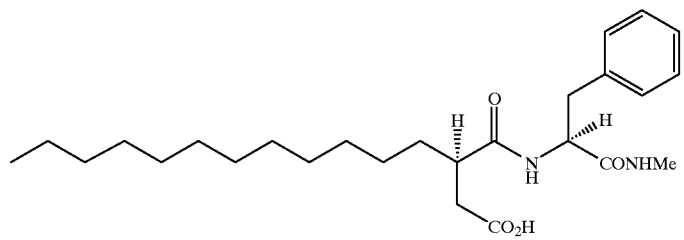

White solid. $^1$H NMR; δ ((CD$_3$)$_2$SO), 8.01 (1H, d, J=8.2 Hz), 7.70 (1H, m), 7.31–7.11 (5H, m, Ph), 4.43 (1H, m), 2.97 (1H, dd, J=5.6, 13.8 Hz), 2.81 (1H, dd, J=8.8, 13.8 Hz), 2.54 (1H, m and 3H, d, J=4.4 Hz), 2.32 (1H, dd, J=7.7, 16.2 Hz), 2.15 (1H, dd, J=6.7, 16.4 Hz) and 1.43–1.02 (22H, m), $^{13}$C NMR; δ (CD$_3$)$_2$SO, 173.7, 173.3, 171.2, 138.0, 129.0, 127.9, 126.1, 53.9, 41.5, 37.4, 36.3, 32.0, 31.3, 29.0, 28.9, 28.7, 26.4, 25.4, 22.1 and 13.7. Found C 70.00, H 9.47, N 6.27%; C$_{26}$H$_{42}$N$_2$O$_4$ requires C 69.92, H 9.48, N 6.27%.

Biological Example

The potency of compounds of the invention as inhibitors of collagenase was determined by the procedure of Cawston and Barrett, (*Anal. Biochem.*, 99, 340–345, 1979), hereby incorporated by reference, whereby a 1 mM solution of the compound being tested, or a dilution thereof, was incubated at 37° for 16 hours with collagen and collagenase (buffered with 25 mM Hepes, pH 7.5 containing 5 mM CaCl$_2$, 0.05% Brij 35 and 0.02% NaN$_3$). The collagen was acetylated $^{14}$C collagen prepared by the method of Cawston and Murphy, (*Methods in Enzymology*, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity (IC$_{50}$). For weak inhibitors, the percentage inhibition (% I) at a concentration of 100 μM is given.

The potency of compounds of the invention as inhibitors of stromelysin was determined by the procedure of Cawston et al, (*Biochem. J.*, 195, 159–165, 1981), hereby incorporated by reference, whereby a 1 mM solution of the compound being tested, or a dilution thereof, was incubated at 37° for 16 hours with stromelysin and $^{14}$C acetylate casein (buffered with 25 mM Hepes, pH 7.5 containing 5 mM CaCl$_2$, 0.05% Brij 35 and 0.02% NaN$_3$). The casein was acetylated $^{14}$C casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity (IC$_{50}$). For weak inhibitors, the percentage inhibition (% I) at a concentration of 100 μM is given.

The potency of compounds of the invention as inhibitors of 72 kDa gelatinase was determined by a procedure based on the method of Sellers et. al, *Biochem. J.*, 171, 493–496 (1979). 72 kDa gelatinase, derived from RPMI-7951 cells was purified by gelatin-agarose chromatography. The enzyme was activated by incubation with aminophenyl mercuric acetate and approximately 0.05 units was incubated with 50 μg [$^{14}$C]-radiolabelled gelatin in an appropriate buffer for 16 hours at 37° C. At the end of the incubation 50 μg bovine serum albumin, together with trichloroacetic acid (final concentration 16%) were added to stop the reaction and to precipitate any undegraded substrate. The reaction tubes were placed on ice for 15 minutes before centrifugation at 10,000 g for 15 minutes to sediment the precipitated substrate. A 200 μl aliquot of the reaction supernatant was removed and the radioactivity determined by liquid scintillation counting. The effect of the inhibitors was determined by reference to a dose response curve. The IC$_{50}$ (the concentration of inhibitor required to cause a 50% decrease in enzyme activity) was obtained by fitting a curve to the data and computing the concentration of inhibitor required to achieve 50% inhibition of the enzyme. For each IC$_{50}$ determination, the effect on gelatinase activity of at least 8 concentrations of the inhibitor were examined. The inhibitors were dissolved and diluted in DMSO.

The potency of compounds of the invention as inhibitors of human PUMP-1 (matrilysin) was assessed as follows. Recombinant human PUMP-1 was expressed in CHO cells and purified by heparin-agarose and Procion Red chromatography. A [$^{14}$C]-casein degradation assay was used to measure PUMP-1 activity. This involved incubation of 0.02 units of the enzyme with 100 μg [$^{14}$C]-casein in an appropriate buffer for 16 hours at 37° C. The incubation was terminated by addition of trichloroacetic acid (final concentration 10%) and the substrate was separated from the TCA-soluble degradation products by centrifugation at 10,000 g for 15 minutes. A 200 μl aliquot of the reaction supernatant was removed and the radioactivity associated with the TCA-soluble products released from casein by PUMP-1 determined by liquid scintillation counting. The effect of the inhibitors was determined by reference to a dose response curve. For each IC$_{50}$ determination, the effect on PUMP-1 activity of at least 8 concentrations of the inhibitor were examined. The inhibitors were dissolved and diluted in DMSO. The IC$_{50}$ (the concentration of inhibitor required to cause a 50% decrease in enzyme activity) was obtained by manual interpolation from the graph. For weak inhibitors, the percentage inhibition (% I) at a concentration of 100 μM is given.

The assay results for the compound of Example 1 and of the comparator compound of Example A are summarised below:

| | IC$_{50}$ (nM) or % Inhibition @ 100 μM | | | |
|---|---|---|---|---|
| Compound | Gelatinase | Collagenase | Stromelysin | PUMP |
| Example 1 | 30 | 0% I | 10% I | 20% I |
| Comparator Example A | 500 | 30% I | 1000 | 10% I |

We claim:

1. A pharmaceutical or veterinary composition comprising a compound of formula I

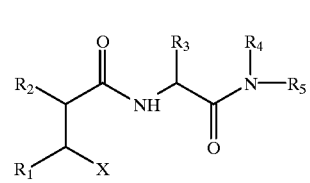

(I)

wherein
X is a —CO$_2$H group;
R$_1$ is hydrogen;
R$_2$ represents a linear saturated or unsaturated C$_{13}$–C$_{24}$ hydrocarbon chain, wherein the hydrocarbon chain
 (i) may be interrupted by one or more non-adjacent —O— or —S— atoms or —C(=O)—, —S(→O)—, —S(=O)$_2$— or N(R$_x$)— groups wherein R$_x$ is hydrogen, methyl or ethyl, provided that the maximum length of the chain is no more than 28 C, O, S and N atoms, and/or
 (ii) may be substituted with one or more groups selected from C$_1$–C$_6$ alkyl, OH, OMe, halogen, NH$_2$, NHCH$_3$, N(CH$_3$)$_2$, CO$_2$H, CO$_2$CH$_3$, COCH$_3$, CHO, CONH$_2$, CONHCH$_3$, CON(CH$_3$)$_2$, CH$_2$OH, NHCOCH$_3$, provided that the maximum length of the chain is no more than 28 C, O, S and N atoms;

R$_3$ is the characterizing side chain of a natural or non-natural α amino acid in which any functional groups may be protected, with the proviso that R$_3$ does not represent hydrogen;

R$_4$ is hydrogen, C$_1$–C$_6$ alkyl, (C$_1$–C$_4$)perfluoroalkyl or a group D-(C$_1$–C$_6$ alkyl) wherein D represents hydroxy, (C$_1$–C$_6$)alkoxy, (C$_1$–C$_6$)alkylthio, acylamino, optionally substituted phenyl or heteroaryl, NH$_2$, or mono or di-(C$_1$–C$_6$) alkyl amino;

R$_5$ is hydrogen or a (C$_1$–C$_6$)alkyl group;

or a salt, hydrate or solvate thereof, and a pharmaceutically or veterinarily acceptable excipient or carrier.

2. A composition as claimed in claim 1 wherein the stereochemistry is in general as follows:

C atom carrying the R$_2$ group —R,

C atom carrying the R$_3$ group —S.

3. A composition as claimed in claim 2 wherein R$_2$ is a linear saturated or unsaturated C$_{13}$–C$_{24}$ hydrocarbon chain, which chain (i) may be interrupted by one or more non-adjacent —O— or —S— atoms;

(ii) may be optionally substituted, and which has a chain length of from 13 to 16 or 14 to 16; or both (i) and (ii).

4. A composition as claimed in claim 2 wherein R$_2$ is tridecyl, tetradecyl, pentadecyl, heptadecyl, octadecyl, nonadecyl, eicosyl, heneicosyl, docosyl, tricosyl, tetracosyl, 13-methoxytridecyl, 3-undecoxypropyl, 4-decoxybutyl, 5-nonoxypentyl, 6-octoxyhexyl, 7-heptaoxylheptyl, or 8-hexaoxyoctyl.

5. A composition as claimed in claim 2 wherein R$_2$ is hexadecyl.

6. A composition as claimed in claim 2 wherein R$_3$ is (C$_1$–C$_6$)alkyl, benzyl, hydroxybenzyl, benzyloxybenzyl, (C$_1$–C$_6$)alkoxybenzyl, or benzyloxy (C$_1$–C$_6$)alkyl group; or the characterizing group of a natural α amino acid, in which any functional group may be protected, any amino group may be acylated, and any carboxyl group present may be amidated; or a group -(Alk)$_n$R$_6$ where Alk is a (C$_1$–C$_6$)alkyl or (C$_2$C$_6$) alkenyl group optionally interrupted by one or more —O—, or —S— atoms or —N(R$_7$)— groups, where R$_7$ is a hydrogen atom or a (C$_1$–C$_6$)alkyl group, n is 0 or 1, and R$_6$ is an optionally substituted cycloalkyl or cycloalkenyl group; or a benzyl group substituted in the phenyl ring by a group of formula —OCH$_2$COR$_8$ where R$_8$ is hydroxyl, amino, (C$_1$–C$_6$)alkoxy, phenyl(C$_1$–C$_6$)alkoxy, (C$_1$–C$_6$) alkylamino, di((C$_1$–C$_6$)alkyl)amino, phenyl (C$_1$–C$_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic((C$_1$–C$_6$)alkyl group, either being unsubstituted or mono- or di-substituted in the heterocyclic ring with halo, nitro, carboxy, (C$_1$–C$_6$)alkoxy, cyano, (C$_1$–C$_6$)alkanoyl, trifluoromethyl (C$_1$–C$_6$)alkyl, hydroxy, formyl, amino, (C$_1$–C$_6$)alkylamino, di-(C$_1$–C$_6$)alkylamino, mercapto, (C$_1$–C$_6$)alkylthio, hydroxy (C$_1$–C$_6$)alkyl, mercapto (C$_1$–C$_6$)alkyl or (C$_1$–C$_6$)alkylphenylmethyl; or a group —CR$_a$R$_b$R$_c$ in which:

each of R$_a$R$_b$R$_c$ is independently hydrogen, (C$_1$–C$_6$) alkyl, (C$_2$–C$_6$)alkenyl, (C$_2$–C$_6$)alkynyl, phenyl (C$_1$–C$_6$)alkyl, (C$_3$–C$_8$)cycloalkyl, the foregoing being subject to the proviso that R$_a$, R$_b$ and R$_c$ are not all hydrogen; or R$_c$ is hydrogen, (C$_1$–C$_6$)alkyl, (C$_2$–C$_6$)alkyl, (C$_2$–C$_6$) alkynyl, phenyl (C$_1$–C$_6$)alkynyl, phenyl (C$_1$–C$_6$) alkyl, or (C$_3$–C$_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring; or R$_a$ and R$_b$ are each independently (C$_1$–C$_6$)alkyl, (C$_2$–C$_6$)alkenyl, (C$_2$–C$_6$)alkynyl, phenyl (C$_1$–C$_6$) alkyl, or a group as defined for R$_c$ below other than hydrogen, or R$_a$ and R$_b$ together with the carbon atom to which they are attached form a 3 to 8 membered cycloalkyl or a 3- to 8- membered heterocyclic ring, and R$_c$ is hydrogen, —OH, —SH, halogen, —CN, —CO$_2$H, (C$_1$–C$_4$)perfluoroalkyl, —CH$_2$OH, —CO$_2$ (C$_1$–C$_6$)alkyl, —O(C$_1$–C$_6$)alkyl, —O(C$_2$–C$_6$)alkenyl, —S (C$_1$–C$_6$)alkyl, —SO (C$_1$–C$_6$)alkyl, —SO$_2$ (C$_1$–C$_6$)alkyl, —S(C$_2$–C$_6$) alkenyl, —SO(C$_2$–C$_6$)alkenyl, —SO$_2$ (C$_2$–C$_6$) alkenyl or a group —Q—W wherein Q represents a bond or —O—, —S—, —SO— or —SO$_2$— and W represents a phenyl, phenylalkyl, (C$_3$–C$_8$)cycloalkyl, (C$_3$–C$_8$)cycloalkylalkyl, (C$_4$–C$_8$)cycloalkenyl, (C$_4$–C$_8$)cycloalkenylalkyl, heteroaryl, or heteroarylalkyl group, which group W may optionally be substituted by one or more substituents independently selected from, hydroxyl, halogen, —CN, —CO$_2$H, —CO$_2$ (C$_1$–C$_6$)alkyl, —CONH$_2$, —CONH (C$_1$–C$_6$) alkyl, —CONH (C$_1$–C$_6$alkyl)$_2$, —CHO, —CH$_2$OH, (C$_1$–C$_4$)perfluoroalkyl, —O (C$_1$–C$_6$)alkyl, —S(C$_1$–C$_6$)alkyl, —SO(C$_1$–C$_6$)alkyl, —SO$_2$ (C$_1$–C$_6$)alkyl, —NO$_2$, —NH$_2$, —NH (C$_1$–C$_6$)alkyl, —N((C$_1$–C$_6$)alkyl)$_2$, —NHCO (C$_1$–C$_6$)alkyl, (C$_1$–C$_6$)alkyl, (C$_2$–C$_6$)alkenyl, (C$_2$–C$_6$)alkynyl, (C$_3$–C$_8$)cycloalklyl, (C$_4$–C$_8$)cycloalkenyl, phenyl or benzyl.

7. A composition as claimed in claim 2 wherein R$_3$ is benzyl, iso-butyl, 1-benzylthio-1-methylethyl, or 1-methylthio-1-methylethyl, or 1-mercapto-1-methylethyl.

8. A composition as claimed in claim 2 wherein R$_3$ is t-butyl.

9. A composition as claimed in claim 2 wherein R$_4$ is C$_1$–C$_6$ alkyl, (C$_1$–C$_4$)perfluoroalkyl or a group D-(C$_1$–C$_6$ alkyl) wherein D represents hydroxy, (C$_1$–C$_6$)alkoxy, (C$_1$–C$_6$)alkylthio, acylamino, optionally substituted phenyl or heteroaryl.

10. A composition as claimed in claim 9 wherein R$_4$ is ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-demethyl-3-ethoxypropyl, 2-ethylthioethyl, 2-acetoxyethyl, N-acetylaminoethyl, 3-(2-pyrrolidone)propyl, or optionally substituted phenylethyl, phenylpropyl, phenylbutyl or phenylpentyl.

11. The composition as claimed in claim 9 wherein R$_4$ is hydrogen or methyl.

12. The composition as claimed in claim 2 wherein $R_5$ is hydrogen or methyl.

13. The composition as claimed in claim 2 wherein the compound is selected from the group consisting of:

3R-(1S-Methylcarbamoyl-2-phenyl-ethylcarbamoyl) nonadecanoic acid (dicyclohexylamine salt);

3R-(1S-Methylcarbamoyl-2-phenyl-ethylcarbamoyl)-nonadecanoic acid (free acid);

3R-(2,2-Dimethyl-1S-methylcarbamoyl-propylcarbamoyl)-nonadecanoic acid;

3R or S-(2-Mercapto-2-methyl-1S-methylcarbamoyl-propylcarbamoyl)-nonadecanoic acid;

3-(1S-tert-Butylcarbamoyl-2,2dimethyl-propylcarbamoyl)-nonadecanoic acid (dicyclohexylamine salt);

3-(2,2-Dimethyl-1S-isopropylcarbamoyl-propylcarbamoyl)-nonadecanoic acid (dicyclohexylamine salt);

3-(1S-Dimethylcarbamoyl-2,2-dimethyl-propylcarbamoyl)-nonadecanoic acid (potassium salt);

2-(2-Methyl-1S-methylcarbamoyl-2-methylsulfanyl-propylcarbamoyl)-nonadecanoic acid;

3-(2-Benzylsulfanyl-2-methyl-1S-methyl-1S-methylcarbamoyl-propylcarbamoyl)-nonadecanoic acid;

3-(1S-Methylcarbamoyl-2-phenyl-ethylcarbamoyl)-heptadecanoic acid;

3-(1S-Methylcarbamoyl-2-phenyl-ethylcarbamoyl)-octadecanoic acid;

3-(1S-Carbamoyl-2,2-dimethyl-propylcarbamoyl)-nonadecanoic acid;

3-(2,2-Dimethyl-1S-methylcarbamoyl-propylcarbamoyl)-heptadecanoic acid;

3-(2,2-Dimethyl-1S-methylcarbamoyl-propylcarbamoyl)-octadecanoic acid;

and salts, solvates or hydrates thereof.

14. A method of treatment of diseases or conditions mediated by MMPs in mammals, which method comprises administering to the mammal an effective amount of a composition as claimed in any one of claims 1–13.

15. The method as claimed in claim 14, wherein the diseases or condition is rheumatoid arthritis, osteoarthritis, periodontitis, gingivitis, corneal ulceration or tumour invasion by secondary metastases.

16. The method as claimed in claim 14, wherein the mammal is human.

* * * * *